United States Patent
Del Guidice et al.

(10) Patent No.: US 8,926,992 B2
(45) Date of Patent: Jan. 6, 2015

(54) MUCOSAL VACCINES WITH CHITOSAN ADJUVANT AND MENINGOCOCCAL ANTIGENS

(75) Inventors: Giuseppe Del Guidice, Siena (IT); Barbara Baudner, Siena (IT)

(73) Assignees: Novartis AG, Basel (CH); Universiteit Leiden, Leiden (NL)

( * ) Notice: Subject to any disclaimer, the term of this patent is extended or adjusted under 35 U.S.C. 154(b) by 636 days.

(21) Appl. No.: 10/514,207

(22) PCT Filed: May 14, 2003

(86) PCT No.: PCT/IB03/02382
§ 371 (c)(1),
(2), (4) Date: Jun. 28, 2005

(87) PCT Pub. No.: WO03/094834
PCT Pub. Date: Nov. 20, 2003

(65) Prior Publication Data
US 2006/0051378 A1    Mar. 9, 2006

Related U.S. Application Data

(60) Provisional application No. 60/380,675, filed on May 14, 2002.

(30) Foreign Application Priority Data
Jan. 30, 2003 (GB) .................................. 0302218.3

(51) Int. Cl.
*A61K 39/095* (2006.01)
*A61K 39/108* (2006.01)

(52) U.S. Cl.
USPC ..................................... 424/249.1; 424/241.1

(58) Field of Classification Search
USPC ...................................................... 424/241.1
See application file for complete search history.

(56) References Cited

U.S. PATENT DOCUMENTS

| | | | |
|---|---|---|---|
| 6,251,401 B1 | 6/2001 | Ceccarini et al. | |
| 6,818,222 B1 | 11/2004 | Barchfeld et al. | |
| 6,884,435 B1 | 4/2005 | O'Hagan et al. | |
| 2001/0048929 A1 | 12/2001 | Chong et al. | |
| 2002/0156033 A1 | 10/2002 | Bratzler et al. | |
| 2003/0039665 A1 | 2/2003 | Illum et al. | |
| 2003/0068336 A1* | 4/2003 | Ryall | 424/250.1 |
| 2003/0147922 A1 | 8/2003 | Capiau et al. | |
| 2006/0051378 A1 | 3/2006 | Guidice et al. | |
| 2007/0196391 A1 | 8/2007 | O'Hagan | |
| 2009/0117147 A1 | 5/2009 | Berthet et al. | |
| 2011/0045017 A1 | 2/2011 | Lian et al. | |

FOREIGN PATENT DOCUMENTS

| | | |
|---|---|---|
| WO | WO-97/20576 A1 | 6/1997 |
| WO | WO-98/58668 A2 | 12/1998 |
| WO | WO 99 42130 A | 8/1999 |
| WO | WO-00/56359 A2 | 9/2000 |
| WO | WO-01/22993 A2 | 4/2001 |
| WO | WO-01/51008 A2 | 7/2001 |
| WO | WO 02 00249 A | 1/2002 |
| WO | WO 02 45741 A | 6/2002 |
| WO | WO-02/058737 A2 | 8/2002 |
| WO | WO 02 077021 A | 10/2002 |
| WO | WO 03 007985 A | 1/2003 |
| WO | WO 03 028661 A | 4/2003 |
| WO | WO-03/047619 A2 | 6/2003 |
| WO | WO-03/094960 A2 | 11/2003 |

OTHER PUBLICATIONS

Ho et al. (Biotechnol. Appl. Biochem. vol. 33, pp. 91-98, 2001).*
Illum et al. "Chitosan as a novel nasal delivery system for vaccines", Advanced Drug Delivery Reviews, No. 51, No. 1-3, Sep. 23, 2001, pp. 81-96, XP001115064.
Van Der Lubben et al. "Chitosan and its derivatives in mucosal drug and vaccine delivery", European Journal of Pharmaceutial Sciences, vol. 14, No. 3, Oct. 201, pp. 201-207, XP001115063.

(Continued)

*Primary Examiner* — Gary B. Nickol
(74) *Attorney, Agent, or Firm* — Morrison & Foerster LLP

(57) ABSTRACT

The invention provides immunogenic compositions comprising (a) a capsular saccharide antigen from serogroup C of *N. meningitidis*, and (b) a chitosan adjuvant. The composition preferably comprises (c) one or more further antigens and/or (d) one or more further adjuvants. The compositions are particularly suitable for mucosal delivery, including intranasal delivery. The invention also provides immunogenic compositions for mucosal delivery comprising capsular saccharides from at least two of serogroups A, C, W135 and Y of *N. meningitidis*. It is preferred that the capsular saccharides in the compositions of the invention are conjugated to carrier protein(s) and/or are oligosaccharides. Conjugated oligosaccharide antigens are particularly preferred.

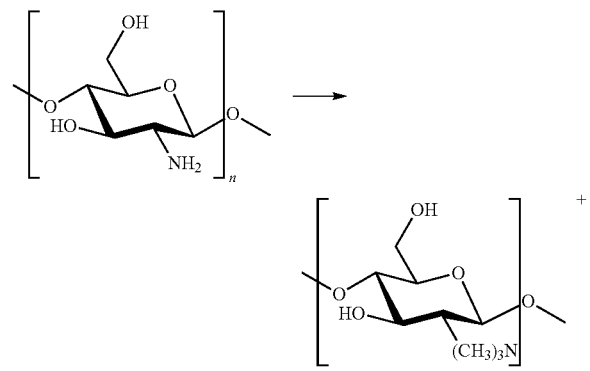

15 Claims, 12 Drawing Sheets

(56) References Cited

OTHER PUBLICATIONS

Ugozzoli et al. "Potency of a genetically detoxified mucosal adjuvant derived from the heat-labile enterotoxin of *Escherichia coli* (LTK63) is not adversely affected by the presence of preexisting immunity to the adjuvant", Journal of Infectious Diseases, vol. 183, No. 2, Jan. 15, 2001, pp. 351-354, XP002264403.

Peltola H: "Meningococcal Vaccines Current Status and Future Possibilities", Drugs, Adis International Ltd, vol. 55, No. 3, Mar. 1998, pp. 347-366, XP008022620.

Baudner et al. "The Concomitant Use of the LTK63 Mucosal Adjuvant and of Chitosan-based Delivery System Enhances the Immunogenicity and Efficacy of Intranasally Administered Vaccines", Vaccine, vol. 21, No. 25-26, Sep. 8, 2003, pp. 3837-3844, XP004446158.

Gizurarson, "Clinically relevant vaccine-vaccine interactions: a guide for practitioners, " BioDrugs. Jun. 1998;9 (6):443-53.

Edelman, "The development and use of vaccine adjuvants," Mol Biotechnol. Jun. 2002;21(2):129-48.

Wuorimaa et al., "Avidity and subclasses of IgG after immunization of infants with an 11-valent pneumococcal conjugate vaccine with or without aluminum adjuvant," J Infect Dis. Nov. 1, 2001;184(9)1211-5. Epub Sep. 25, 2001.

Aucouturier et al., "Adjuvants designed for veterinary and human vaccines," Vaccine. Mar. 21, 2001;19(17-19):2666-72.

Alpar et al., "Intranasal vaccination against plague, tetanus and diphtheria," Advanced Drug Delivery Reviews. 51: 173-201 Elsevier Science B.V. (2001).

Van der Lubben et al., "Trimethyl chitosan chloride (TMC) as a novel excipient for oral and nasal immunisation against diphtheria," S.T.P. Pharma Sciences 12(4): 235-242 (2002).

Aucouturier et al. (2001). "Adjuvants designed for veterinary and human vaccines," Vaccine 19:2666-2672.

Edelman (2002). "The Development and Use of Vaccine Adjuvants," Molecular Biotechnology 21(2):129-148.

Wuorimaa et al. (2001). "Avidity and Subclasses of IgG after Immunization of Infants with an 11-Valent Pneumococcal Conjugate Vaccine with or without Aluminum Adjuvant," The Journal of Infectious Diseases 184:1211-5.

Baudner et al. (Sep. 2002). "Enhancement of protective efficacy following intranasal immunization with vaccine plus a nontoxic LTK63 mutant delivered with nanoparticles," Infection and Immunity 70(9):4785-4790.

Bruce et al. (1990) "Diphtheria toxin and its ADP-ribosyltransferase-defective homologue CRM197 possess deoxyribonuclease activity," PNAS 87:2995-2998.

Crooy et al. (1979). "Analysis of a bivalent meningococcal vaccine," Ann. Soc. Beige Med. Trop. 59:267-277.

Douce et al (1999) "Genetically detoxified mutants of heat-labile toxin from *Escherichia coli* are able to act as oral adjuvants," Infect Immun 67(9):4400-4406.

Eskola et al. (Dec. 11, 1999). "Combined vaccination of Haemophilus influenzae type b conjugate and diphtheria-tetanus-pertussis containing acellular pertussis," Lancet 354(9195):2063-8.

Giuliani et al. (1998). "Mucosal adjuvanticity and immunology of LTR72, a novel mutant of *Escherichia coli* heat-labile enterotoxin with partial knockout of ADP-ribosyltransferase activity," J Exp Med 187(7):1123-1132.

Huo et al. (Dec. 2005). "Induction of protective serum meningococcal bactericidal and diphtheria-neutralizing antibodies and mucosal immunoglobulin A in volunteers by nasal insufflations of the *Neisseria meningitidis* serogroup C polysaccharide-CRM197 conjugate vaccine mixed with chitosan," Infect Immun 73(12):8256-8265.

Kelly et al. (Oct. 2004). "Haemophilus influenzae type b conjugate vaccines," Immunol 113(2):163-74.

McNeela et al. (2001). "A mucosal vaccine against diphtheria: formulation of cross reaction material (CRM197) of diphtheria toxin with chitosan enhances local and systemic antibody and Th2 responses following nasal delivery," Vaccine 19(9-10):1188-1198.

McNeela et al. (2001). "Manipulating the immune system: humoral versus cell-mediated immunity," Adv Drug Deliv Rev 51(1-3):43-54.

Porro et al. (1986). "A molecular model of artificial glycoprotein with predetermined multiple immunodeterminants for gram-positive and gram-negative encapsulated bacteria," Molec Immunol 23(4):385-392.

Ryan et al (1999). "Mutants of *Escherichia coli* heat-labile toxin act as effective mucosal adjuvants for nasal delivery of an acellular pertussis vaccine: differential effects of the nontoxic AB complex and enzyme activity on Th1 and Th2 cells," Infect Immun 67(12):6270-6280.

Ryan et al. (2000). "Modulation of innate and acquired immune responses by *Eschericia coli* heat-labile toxin: distinct pro- and anti-inflammatory effects of the nontoxic AB complex and the enzyme activity," J Immunol 165(10):5750-5759.

Ryan et al. (1998). "Pertussis toxin potentiates Th1 and Th2 responses to co-injected antigen: adjuvant action is associated with enhanced regulatory cytokine production and expression of the co-stimulatory molecules B7-1, B7-2, and CD28," International Immunology 10(4):651-662.

Ugozzoli et al. (2002). "Combinations of protein polysaccharide conjugate vaccines for intranasal immunization," J Infect Dis 186(9):1358-1361.

* cited by examiner

MUCOSAL VACCINES WITH CHITOSAN ADJUVANT AND MENINGOCOCCAL ANTIGENS

TECHNICAL FIELD

This invention is in the field of vaccines, particularly against meningococcal infection and disease.

BACKGROUND ART

*Neisseria meningitidis* is a Gram-negative human pathogen [e.g. see Chapter 28 of ref. 1] which causes bacterial meningitis. It is closely related to *N. gonorrhoeae*, although one feature that clearly differentiates meningococcus is the presence of a polysaccharide capsule that is present in all pathogenic meningococci.

Based on the organism's capsular polysaccharide, twelve serogroups of *N. meningitidis* have been identified (A, B, C, H, I, K, L, 29E, W135, X, Y and Z). Group A is most common cause of epidemic disease in sub-Saharan Africa. Serogroups B & C are responsible for the vast majority of cases in developed countries, with the remaining cases being caused by serogroups W135 & Y.

As well as being used for classification, the capsular polysaccharide has been used for vaccination. An injectable tetravalent vaccine of capsular polysaccharides from serogroups A, C, Y & W135 has been known for many years [2, 3] and is licensed for human use. Although effective in adolescents and adults, it induces a poor immune response and short duration of protection and cannot be used in infants [e.g. 4]. The polysaccharides in this vaccine are unconjugated and are present at a 1:1:1:1 weight ratio [5]. MENCEVAX ACWY™ and MENOMUNE™ both contain 50 μg of each purified polysaccharide once reconstituted from their lyophilised forms.

Conjugated serogroup C oligosaccharides have also been approved for human use [e.g. MENJUGATE™; ref.6]. There remains, however, a need for improvements in conjugate vaccines against serogroups A, W135 and Y, and in their manufacture. That need is addressed by the products, processes and uses disclosed in reference 8, but there remains scope for further modifications and improvements, particularly in relation to the delivery and formulation.

DISCLOSURE OF THE INVENTION

The invention provides an immunogenic composition, comprising (a) a capsular saccharide antigen from serogroup C of *N. meningitidis*, and (b) a chitosan adjuvant. The composition preferably comprises (c) one or more further antigens and/or (d) one or more further adjuvants.

The invention also provides an immunogenic composition for mucosal delivery, comprising capsular saccharides from at least two of serogroups A, C, W135 and Y of *N. meningitidis*.

It is preferred that the capsular saccharides in the compositions of the invention are conjugated to carrier protein(s) and/or are oligosaccharides. Conjugated oligosaccharide antigens (FIG. 1) are particularly preferred.

Capsular Saccharide Antigen from Serogroup C Meningococcus

The capsular saccharide of serogroup C of *N. meningitidis* has been widely used as an antigen. The active ingredient of Menjugate™, for instance, is an oligosaccharide fragment of the capsular polysaccharide, conjugated to $CRM_{197}$ carrier protein.

Where a composition of the invention includes a capsular saccharide antigen from serogroup C of *N. meningitidis*, it is thus preferred to use an oligosaccharide fragment of the capsular polysaccharide and/or to conjugate the saccharide antigen to a carrier protein. Particularly preferred MenC saccharide antigens are disclosed in references 6 & 9.

Further details of oligosaccharide production and conjugation are given below.

Saccharide Mixtures

The compositions of the invention can comprise capsular saccharides from at least two (i.e. 2, 3 or 4) of serogroups A, C, W135 and Y of *N. meningitidis*.

Mixtures of saccharides from more than one serogroup of *N. meningitidis* are preferred e.g. compositions comprising saccharides from serogroups A+C, A+W135, A+Y, C+W135, C+Y, W135+Y, A+C+W135, A+C+Y, C+W135+Y, A+C+W135+Y, etc. It is preferred that the protective efficacy of individual saccharide antigens is not removed by combining them, although actual immunogenicity (e.g. ELISA titres) may be reduced.

Preferred compositions comprise saccharides from serogroups C and Y. Other preferred compositions comprise saccharides from serogroups C, W135 and Y.

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher).

Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower).

Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1.

Purification of Capsular Polysaccharides

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 10].

A more preferred process [8], however, involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [11]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

The polysaccharide may be chemically modified. For instance, it may be modified to replace one or more hydroxyl groups with blocking groups. This is particularly useful for serogroup A [12].

Oligosaccharides

The capsular saccharides will generally be in the form of oligosaccharides. These are conveniently formed by fragmentation of purified capsular polysaccharide (e.g. by hydrolysis, in mild acid, or by heating), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [13].

If hydrolysis is performed, the hydrolysate will generally be sized in order to remove short-length oligosaccharides. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines [e.g. ref. 14] and is a well known technique [e.g. reviewed in refs. 15 to 23, etc.].

Preferred carrier proteins are bacterial toxins or toxoids, such as diphtheria or tetanus toxoids. The $CRM_{197}$ diphtheria toxoid [24, 25, 26] is particularly preferred. Other suitable carrier proteins include the *N. meningitidis* outer membrane protein [27], synthetic peptides [28, 29], heat shock proteins [30, 31], pertussis proteins [32, 33], cytokines [34], lymphokines [34], hormones [34], growth factors [34], artificial proteins comprising multiple human $CD4^+$ T cell epitopes from various pathogen-derived antigens [35], protein D from *H. influenzae* [36], toxin A or B from *C. difficile* [37], etc.

Within a composition of the invention, it is possible to use more than one carrier protein. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [38]. For example, a single carrier protein might have conjugated to it saccharides from serogroups A and C.

Conjugates with a saccharide:protein ratio (w/w) of between 0.5:1 (i.e. excess protein) and 5:1 (i.e. excess saccharide) are preferred, and those with a ratio between 1:1.25 and 1:2.5 are more preferred.

Conjugates may be used in conjunction with free carrier protein [39].

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [40, 41, etc.]). Other suitable techniques use carbodiimides, hydrazides, active esters, norborane, p-nitrobenzoic acid, N-hydroxysuccinimide, S-NHS, EDC, TSTU; see also the introduction to reference 21).

Linkages via a linker group may be made using any known procedure, for example, the procedures described in references 42 and 43. One type of linkage involves reductive amination of the polysaccharide, coupling the resulting amino group with one end of an adipic acid linker group, and then coupling a protein to the other end of the adipic acid linker group [19, 44, 45]. Other linkers include B-propionamido [46], nitrophenyl-ethylamine [47], haloacyl halides [48], glycosidic linkages [49], 6-aminocaproic acid [50], ADH [51], $C_4$ to $C_{12}$ moieties [52] etc. As an alternative to using a linker, direct linkage can be used. Direct linkages to the protein may comprise oxidation of the polysaccharide followed by reductive amination with the protein, as described in, for example, references 53 and 54.

A process involving the introduction of amino groups into the saccharide (e.g. by replacing terminal =O groups with $-NH_2$) followed by derivatisation with an adipic diester (e.g. adipic acid N-hydroxysuccinimido diester) and reaction with carrier protein is preferred.

After conjugation, free and conjugated saccharides can be separated. There are many suitable methods, including hydrophobic chromatography, tangential ultrafiltration, diafiltration etc. [see also refs. 55 & 56, etc.].

Where the composition of the invention includes a conjugated oligosaccharide, it is preferred that oligosaccharide preparation precedes conjugation.

Preparation of Compositions of the Invention

Where compositions of the invention include more than one type of capsular saccharide, they are preferably prepared separately (including any fragmentation, conjugation, etc.) and then admixed to give a composition of the invention.

Where the composition comprises capsular saccharide from serogroup A, however, it is preferred that the serogroup A saccharide is not combined with the other saccharide(s) until shortly before use, in order to minimise the potential for hydrolysis. This can conveniently be achieved by having the serogroup A component in lyophilised form and the other serogroup component(s) in liquid form, with the liquid component being used to reconstitute the lyophilised component when ready for use.

A composition of the invention may thus be prepared from a kit comprising: (a) capsular saccharide from *N. meningitidis* serogroup A, in lyophilised form; and (b) capsular saccharide(s) from one or more (e.g. 1, 2, 3) of *N. meningitidis* serogroups C, W135 and Y, in liquid form. The invention also provides a method for preparing a composition of the invention, comprising mixing a lyophilised capsular saccharide from *N. meningitidis* serogroup A with capsular saccharide(s) from one or more (e.g. 1, 2, 3) of *N. meningitidis* serogroups C, W135 and Y, wherein said one or more saccharides are in liquid form.

The invention also provides a composition of the invention, comprising capsular saccharide(s) from *N. meningitidis* serogroups C, W135 and Y, wherein saccharides are in liquid form. This composition may be packaged with a lyophilised serogroup A saccharide antigen, for reconstitution, or it may be used as a composition on its own e.g. where immunisation against serogroup A is not desired.

Presentation of Compositions of the Invention

Compositions of the invention may be presented and packaged in various ways.

Where compositions are for injection, they may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form for solution or suspension in liquid vehicles prior to injection.

Where a composition of the invention is to be prepared extemporaneously prior to use (e.g. where serogroup A saccharide is presented in lyophilised form) and is presented as a kit, the kit may comprise two vials, or it may comprise one ready-filled syringe and one vial, with the contents of the syringe being used to reactivate the contents of the vial prior to injection.

However, preferred compositions are for mucosal delivery. Of the various mucosal delivery options available, the intranasal route is the most practical as it offers easy access with relatively simple devices that have already been mass produced. The composition of the invention is thus preferably adapted for and/or packaged for intranasal administration, such as by nasal spray, nasal drops, gel or powder [e.g. refs 57 & 58].

Alternative routes for mucosal delivery of the composition are oral, intragastric, pulmonary, intestinal, transdermal, rectal, ocular, and vaginal routes. The composition of the invention may thus be adapted for and/or packaged for mucosal administration [e.g. see refs. 59, 60 & 61]. Where the composition is for oral administration, for instance, it may be in the form of tablets or capsules (optionally enteric-coated), liquid, transgenic plant material, drops, inhaler, aerosol, enteric coating, suppository, pessary, etc. [see also ref. 62, and Chapter 17 of ref. 73].

Whatever the route of delivery, compositions of the invention are preferably packaged in unit dose form. Effective doses can be routinely established. A typical human dose of the composition for injection or for intranasal use has a volume between 0.1-0.5 ml e.g. two 100 μl sprays, one per nostril.

Within each dose, the amount of an individual saccharide antigen will generally be between 1-50 μg (measured as mass of saccharide), with about 10 μg of each being preferred.

Compositions of the invention are preferably sterile. They are preferably pyrogen-free. They are preferably buffered e.g. at between pH 6 and pH 8, generally around pH 7. Where a composition comprises an aluminium hydroxide salt, it is preferred to use a histidine buffer [63].

Adjuvants

The compositions will generally include one or more adjuvants. The adjuvant(s) may be added to saccharides before and/or after they are admixed to form a composition of the invention, but it is preferred to combine adjuvant with a saccharide antigen prior to admixing of different saccharides. However, it is not necessary that each saccharide must be adjuvanted prior to such admixing. Excess adjuvant can be included in one saccharide preparation such that, when further unadjuvanted saccharide antigen(s) is/are added, the excess is diluted to a desired final concentration. In one particular embodiment, where the composition of the invention is prepared from a lyophilised antigen (e.g. a lyophilised serogroup A component) it may be preferred not to include an adjuvant in the lyophilised material.

For mucosal delivery, it is preferred to use a mucosal adjuvant. Mucosal adjuvants include, but are not limited to: (A) $E.$ $coli$ heat-labile enterotoxin ("LT"), or detoxified mutants thereof [e.g. Chapter 5 of ref. 64]; (B) cholera toxin ("CT"), or detoxified mutants thereof [e.g. Chapter 5 of ref. 64]; or (C) microparticles (i.e. a particle of ~100 nm to ~50 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone etc., such as poly(lactide-co-glycolide) etc.) optionally treated to have a negatively-charged surface (e.g. with SDS) or a positively-charged surface (e.g. with a cationic detergent, such as CTAB); (D) a polyoxyethylene ether or a polyoxyethylene ester [65]; (E) a polyoxyethylene sorbitan ester surfactant in combination with an octoxynol [66] or a polyoxyethylene alkyl ether or ester surfactant in combination with at least one additional non-ionic surfactant such as an octoxynol [67]; (F) chitosan [e.g. 68]; (G) an immunostimulatory oligonucleotide (e.g. a CpG oligonucleotide) and a saponin [69]; (H) liposomes [chapters 13 & 14 of ref. 73]; (I) monophosphoryl lipid A mimics, such as aminoalkyl glucosaminide phosphate derivatives e.g. RC-529 [70]; (J) polyphosphazene (PCPP); (K) a bioadhesive [71] such as esterified hyaluronic acid microspheres [72] or a mucoadhesive selected from the group consisting of cross-linked derivatives of poly(acrylic acid), polyvinyl alcohol, polyvinyl pyrollidone, polysaccharides and carboxymethylcellulose. Other mucosal adjuvants are also available [e.g. see chapter 7 of ref. 73].

In addition to the mucosal adjuvants given above, the compositions of the invention may include one or more further antigens from the following group: (A) aluminium salts (alum), such as aluminium hydroxides (including oxyhydroxides), aluminium phosphates (including hydroxyphosphates), aluminium sulfate, etc [Chapters 8 & 9 in ref. 73]; (B) oil-in-water emulsion formulations (with or without other specific immunostimulating agents such as muramyl peptides [Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.] or bacterial cell wall components), such as for example (a) MF59™ [Chapter 10 in ref. 73; 74, 75], containing 5% Squalene, 0.5% TWEEN®80 (polyoxyethylenesorbitan, monooleate), and 0.5% SPAN®85 (sorbitan trioleate)(optionally containing MTP-PE) formulated into submicron particles using a microfluidizer, (b) SAF, containing 10% Squalane, 0.4% TWEEN®80 (polyoxyethylenesorbitan, monooleate), 5% PLURONIC™ L121-blocked polymer (block copolymer of propylene oxide and ethylene oxide), and thr-MDP either microfluidized into a submicron emulsion or vortexed to generate a larger particle size emulsion, and (c) RIBI™ adjuvant system (RAS), (Ribi Immunochem, Hamilton, MT) containing 2% Squalene, 0.2% TWEEN®80 (polyoxyethvlenesorbitan, monooleate), and one or more bacterial cell wall components from the group consisting of monophosphorylipid A (MPL), trehalose dimycolate (TDM), and cell wall skeleton (CWS), preferably MPL+CWS (DETOX™); (C) saponin adjuvants [chapter 22 of ref. 73], such as QS21 or STIMULON™ (Cambridge Bioscience, Worcester, Mass.), either in simple form or in the form of particles generated therefrom such as ISCOMs (immunostimulating complexes; chapter 23 of ref 73), which ISCOMS may be devoid of additional detergent e.g. ref. 76; (D) Complete Freund's Adjuvant (CFA) and Incomplete Freund's Adjuvant (IFA); (E) cytokines, such as interleukins (e.g. IL-1, IL-2, IL-4, IL-5, IL-6, IL-7, IL-12 [77], etc.), interferons (e.g. gamma interferon), macrophage colony stimulating factor (M-CSF), tumor necrosis factor (TNF), etc.; (F) monophosphoryl lipid A (MPL) or 3-O-deacylated MPL (3dMPL) e.g. refs. 78 & 79 optionally in the substantial absence of alum when used with pneumococcal saccharides e.g. ref. 80; (G) combinations of 3dMPL with, for example, QS21 and/or oil-in-water emulsions e.g. refs 81, 82 & 83; (H) oligonucleotides comprising CpG motifs i.e. containing at least one CG dinucleotide, with 5-methylcytosine optionally being used in place of cytosine; (I) an immunostimulant and a particle of metal salt e.g. ref 84; (J) a saponin and an oil-in-water emulsion e.g. ref.85; (K) a saponin (e.g. QS21)+3dMPL+IL-12 (optionally+a sterol) e.g. ref 86; (L) double-stranded RNA; (M) other substances that act as immunostimulating agents to enhance the effectiveness of the composition [e.g. chapter 7 of ref 73].

Where an aluminium phosphate it used, it is possible to adsorb one or more of the saccharides to the aluminium salt, but it is preferred not to do so, and this is favoured by including free phosphate ions in solution (e.g. by the use of a phosphate buffer). Where an aluminium hydroxide is used, it is preferred to adsorb the saccharides to the salt. The use of aluminium hydroxide as an adjuvant may be preferred for saccharide from serogroup A.

Preferred mucosal adjuvants are chitosan and detoxified mutants of bacterial toxins (particularly LT.) These can be used alone, or can advantageously be used in combination, as co-administration allows lower doses of the toxin to be used, thereby improving safety.

Chitosan

Chitosan is known for use as an adjuvant [e.g. refs. 87 to 98], particularly for mucosal (e.g. intranasal) use. Chitosan (FIG. 11) is a N-deacetylated derivative of the exoskeletal polymer chitin (FIG. 12), although the N-deacetylation is almost never complete. The deacetylation means that, unlike chitin, chitosan is soluble in dilute aqueous acetic and formic acids. Chitosan has also found wide applicability in non-vaccine pharmaceutical fields [99].

The repeating glucosamine monomer of chitosan contains an amine group. This group may exist as free amine ($-NH_2$) or as cationic amine ($-NH_3^+$), with protonation affecting the polymer's solubility. The amine groups are chemically active and can be substituted. Of particular interest for the invention, the amine groups can be substituted with one or more alkyl group ('A' e.g. methyl, ethyl, propyl, butyl, pentyl, etc.) e.g. $-NHA$, $-NH_2A^+$, $-NA^1A^2$, $-NHA^1A^{2+}$, $-NA^1A^2A^{3+}$. Preferred derivatives are tri-alkylated and particularly preferred derivatives are trimethylated (i.e. trimethylchitosan, or 'TMC'—FIG. 13). These derivatives much higher aqueous solubility than unmodified chitosan over a broader pH range.

It is not necessary for every amine in the chitosan polymer to be substituted in this way. The degree of substitution along the length of the chitosan chain can be determined by $^1$H-NMR and can be controlled by means of the number and duration of reaction steps [100]. It is preferred that at least 10% (e.g. at least 20%, 30%, 40%, 50%, 60%, 70%, 80%, 90%, 95% or more) of monomers have a substituted amine.

There are 2 main reasons why it is rare that 100% of monomers in the chitosan will carry an alklyated amine. First, the substitution reaction will not usually be 100% efficient. Second, it is rare to find chitosan in which 100% of the monomer units carry amine groups because deacetylation of chitin is not usually 100% efficient. Alkylated chitosan derivatives used in the invention may therefore have amide and/or non-alkylated groups on some monomer units, and chitosan may possess some amide groups. Chitosan and derivatives used with the invention are preferably at least 75% deacetylated.

Chitosans come in a variety of molecular weights e.g. from oligosaccharides with molecular weight around 5,000-10,000 to polymers of high molecular weight (e.g. 600,000-1,000,000).

Where a cationic chitosan or derivative is used, it will be in the form of a salt e.g. chloride or lactate.

The chitosan or derivative can take various physical forms e.g in solution, as a powder, or in particulate form. Particulate forms are preferred, including microparticles, which may be cross-linked or non-cross-linked and may be formed conveniently by spray-drying [101, 102]. Other physical forms include gels, beads, films, sponges, fibres, emulsions, etc.

The term "chitosan" as used with reference to the compositions, processes, methods and uses of the invention includes all these forms and derivatives of chitosan.

Detoxified Mutant Toxins

ADP-ribosylating bacterial exotoxins which catalyse the transfer of an ADP-ribose unit from $NAD^+$ to a target protein are widely known. Examples include diphtheria toxin (*Corynebacterium diphtheriae*), exotoxin A (*Pseudomonas aeruginosa*), cholera toxin (CT; *Vibrio cholerae*), heat-labile enterotoxin (LT; *E. coli*) and pertussis toxin (PT). Further examples are in references 103 & 104.

The toxins are typically divided into two functionally distinct domains—A and B. The A subunit is responsible for the toxic enzymatic activity, whereas the B subunit is responsible for cellular binding. The subunits might be domains on the same polypeptide chain, or might be separate polypeptide chains. The subunits may themselves be oligomers e.g. the A subunit of CT consists of $A_1$ and $A_2$ which are linked by a disulphide bond, and its B subunit is a homopentamer. Typically, initial contact with a target cell is mediated by the B subunit and then subunit A alone enters the cell.

The toxins are typically immunogenic, but their inclusion in vaccines is hampered by their toxicity. To remove toxicity without also removing immunogenicity, the toxins have been treated with chemicals such as glutaraldehyde or formaldehyde. A more rational approach relies on site-directed mutagenesis of key active site residues to remove toxic enzymatic activity whilst retaining immunogenicity [e.g. refs. 105 (CT and LT), 106 (PT), 64 etc.]. Current acellular whooping cough vaccines include a form of pertussis toxin with two amino acid substitutions ($Arg^9 \rightarrow Lys$ and $Glu^{129} \rightarrow Gly$; 'PT-9K/129G' [107]).

As well as their immunogenic properties, the toxins have been used as adjuvants. Parenteral adjuvanticity was first observed in 1972 [108] and mucosal adjuvanticity in 1984 [109]. It was surprisingly found in 1993 that the detoxified forms of the toxins retain adjuvanticity [110].

The compositions of the invention include a detoxified ADP-ribosylating toxin. The toxin may be diphtheria toxin, *Pseudomonas* exotoxin A or pertussis toxin, but is preferably cholera toxin (CT) or, more preferably, *E. coli* heat-labile enterotoxin (LT). Other toxins which can be used are those disclosed in reference 104 (SEQ IDs 1 to 7 therein, and mutants thereof).

Detoxification of these toxins without loss of immunogenic and/or adjuvant activity can be achieved by any suitable means, with mutagenesis being preferred. Mutagenesis may involve one or more substitutions, deletions and/or insertions.

Preferred detoxified mutants are LT having a mutation at residue Arg-7 (e.g. a Lys substitution); CT having a mutation at residue Arg-7 (e.g. a Lys substitution); CT having a mutation at residue Arg-11 (e.g. a Lys substitution); LT having a mutation at Val-53; CT having a mutation at Val-53; CT having a mutation at residue Ser-61 (e.g. a Phe substitution); LT having a mutation at residue Ser-63 (e.g. a Lys or Tyr substitution) [e.g. Chapter 5 of ref. 11-K63; ref. 112-Y63); CT having a mutation at residue Ser-63 (e.g. a Lys or Tyr substitution); LT having a mutation at residue Ala-72 (e.g. an Arg substitution) [113-R72]; LT having a mutation at Val-97; CT having a mutation at Val-97; LT having a mutation at Tyr-104; CT having a mutation at Tyr-104; LT having a mutation at residue Pro-106 (e.g. a Ser substitution); CT having a mutation at residue Pro-106 (e.g. a Ser substitution); LT having a mutation at Glu-112 (e.g. a Lys substitution); CT having a mutation at Glu-112 (e.g. a Lys substitution); LT having a mutation at residue Arg-192 (e.g. a Gly substitution); PT having a mutation at residue Arg-9 (e.g. a Lys substitution); PT having a mutation at Glu-129 (e.g. a Gly substitution); and any of the mutants disclosed in reference 105.

These mutations may be combined e.g. Arg-9-Lys+Glu-129-Gly in PT, or LT with both a D53 and a K63 mutation, etc.

LT with a mutation at residue 63 or 72 is a preferred detoxified toxin. The LT-K63 and LT-R72 toxins are particularly preferred [114].

It will be appreciated that the numbering of these residues is based on prototype sequences and that, for example, although Ser-63 may not actually be the 63rd amino acid in a given LT variant, an alignment of amino acid sequences will reveal the location corresponding to Ser-63.

The detoxified toxins may be in the form of A and/or B subunits as appropriate for adjuvant activity.

Further Components of the Compositions

In addition to meningococcal saccharide antigens, compositions of the invention may include meningococcal protein antigens. It is preferred to include proteins from serogroup B of *N. meningitidis* (e.g. refs. 15 to 120] or OMV preparations [e.g. refs. 121 to 124 etc.].

Non-meningococcal and non-neisserial antigens, preferably ones that do not diminish the immune response against the meningococcal components, may also be included. Ref. 125, for instance, discloses combinations of oligosaccharides from *N. meningitidis* serogroups B and C together with the Hib saccharide. Antigens from pneumococcus, hepatitis A virus, hepatitis B virus, *B. pertussis*, diphtheria, tetanus, *Helicobacter pylori*, polio and/or *H. influenzae* are preferred. Particularly preferred non-neisserial antigens include:

antigens from *Helicobacter pylori* such as CagA [126 to 129), VacA [130, 131], NAP [132, 133, 134], HopX [e.g. 135], HopY [e.g. 135] and/or urease.

a saccharide antigen from *Streptococcus pneumoniae* [e.g. 136, 137, 138].

an antigen from hepatitis A virus, such as inactivated virus [e.g. 139, 140].

an antigen from hepatitis B virus, such as the surface and/or core antigens [e.g. 140, 141], with surface antigen preferably being adsorbed onto an aluminium phosphate [142].

a saccharide antigen from *Haemophilus influenzae* B [e.g. 9], preferably non-adsorbed or adsorbed onto an aluminium phosphate [143].

an antigen from hepatitis C virus [e.g. 144].

an antigen from *N. gonorrhoeae* [e.g. 115 to 118].

an antigen from *Chlamydia pneumoniae* [e.g. refs. 145 to 146, 147, 148, 149, 150, 151].

an antigen from *Chlamydia trachomatis* [e.g. 152].

an antigen from *Porphyromonas gingivalis* [e.g. 153].

polio antigen(s) [e.g. 154, 155] such as IPV.

rabies antigen(s) [e.g. 156] such as lyophilised inactivated virus [e.g. 157, RabAvert™].

measles, mumps and/or rubella antigens [e.g. chapters 12, 13 & 17 of ref. 1].

influenza antigen(s) [e.g. chapter 21 of ref.1], such as the haemagglutinin and/or neuraminidase surface proteins.

an antigen from *Moraxella catarrhalis* [e.g. 158].

an antigen from *Streptococcus agalactiae* (group B streptococcus) [e.g. 159, 160].

an antigen from *Streptococcus pyogenes* (group A streptococcus) [e.g. 160, 161, 162].

an antigen from *Staphylococcus aureus* [e.g. 163].

antigen(s) from a paramyxovirus such as respiratory syncytial virus (RSV [164, 165]) and/or parainfluenza virus (PIV3 [166]).

an antigen from *Bacillus anthracis* [e.g. 167, 168, 169].

an antigen from a virus in the flaviviridae family (genus *flavivirus*), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

a tetanus toxoid [e.g. chapter 18 of ref. 1]

pertussis holotoxin (PT) and filamentous haemagglutinin (FHA) from *B. pertussis*, optionally also in combination with pertactin and/or agglutinogens 2 and 3 [e.g. refs. 170 & 171].

cellular pertussis antigen.

The mixture may comprise one or more of these further antigens, which may be detoxified where necessary (e.g. detoxification of pertussis toxin by chemical and/or genetic means).

Where a diphtheria antigen is included in the mixture it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the mixture will typically be present at a concentration of at least 1 µg/ml each. In general, the concentration of any given antigen will be sufficient to elicit an immune response against that antigen.

It may be preferred not to include all three of (1) a meningococcal saccharide, (2) an antigen which induces an immune response against *Haemophilus influenzae*, and (3) an antigen which induces an immune response against *Streptococcus pneumoniae* together in the composition of the invention. If these three antigens are included in the same composition, however, it is preferred that the composition includes an alkylated derivative of chitosan (e.g. trimethylchitosan) as an adjuvant.

As an alternative to using proteins antigens in the mixture, nucleic acid encoding the antigen may be used. Protein components of the mixture may thus be replaced by nucleic acid (preferably DNA e.g. in the form of a plasmid) that encodes the protein. Similarly, compositions of the invention may comprise proteins which mimic saccharide antigens e.g. mimotopes [172] or anti-idiotype antibodies. These may replace individual saccharine components, or may supplement them. As an example, the vaccine may comprise a peptide mimic of the MenC [173] or the MenA [174] capsular polysaccharide in place of the saccharide itself.

Compositions of the invention may comprise detergent (e.g. a TWEEN® such as TWEEN®80 (polyoxyethylenesorbitan, monooleate)) at low levels (e.g., <0.01%). Compositions of the invention may comprise a sugar alcohol (e.g. mannitol) or trehalose e.g. at around 15 mg/ml, particularly if they are to be lyophilized or if they include material which has been reconstituted from lyophilised material.

Immunogenicity

Compositions of the invention are immunogenic. Preferred immunogenic compositions are vaccines. Vaccines according to the invention may either be prophylactic (i.e. to prevent infection) or therapeutic (i.e. to treat disease after infection), but will typically be prophylactic.

Immunogenic compositions and vaccines of the invention will, in addition to the meningococcal saccharides, typically comprise 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, trehalose [175], lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in ref. 176.

Immunogenic compositions used as vaccines comprise an immunologically effective amount of saccharide antigen, as well as any other of the above-mentioned components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Immunogenicity of compositions of the invention can be determined by administering them to test subjects (e.g. children 12-16 months age, or animal models [177]) and then determining standard parameters including serum bactericidal antibodies (SBA) and ELISA titres (GMT) of total and high-avidity anti-capsule IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Administration of Compositions of the Invention

As mentioned above, compositions of the invention may be administered by various routes, including parenteral and mucosal. A preferred route of parenteral administration is injection. Injection may be subcutaneous, intraperitoneal, intravenous or intramuscular. Intramuscular administration to the thigh is preferred. Needle-free injection may be used. A preferred route of mucosal administration is intranasal. Transdermal or transcutaneous administration is also possible (e.g. see ref. 178).

Administration may be a single dose schedule or a multiple dose schedule. A primary dose schedule may be followed by a booster dose schedule. Suitable timing between priming and boosting can be routinely determined.

Administration will generally be to an animal and, in particular, human subjects can be treated. The compositions are particularly useful for vaccinating children and teenagers.

Medical Methods and Uses

The invention provides a method of raising an immune response in a patient, comprising administering to the patient a composition of the invention. The immune response is preferably protective against meningococcal disease, and may comprise a humoral immune response and/or a cellular immune response. The immune response and/or the administration is/are preferably both mucosal.

The patient is preferably a child. A further preferred class of patient is an adult woman, and particularly a woman of child-bearing age or a pregnant woman. Compositions of the invention are particularly suited for passively immunising children via the maternal route.

The method may raise a booster response, in a patient that has already been primed against *N. meningitidis*.

The invention also provides the use of capsular saccharides from at least two of serogroups A, C, W135 and Y of *N. meningitidis*, wherein said capsular saccharides are conjugated to carrier protein(s) and/or are oligosaccharides, in the manufacture of a medicament for intranasal delivery to an animal in order to raise an immune response. The invention also provides the use of (1) a capsular saccharide from at least one of serogroups A, C, W135 and Y of *N. meningitidis*, wherein said capsular saccharides are conjugated to carrier protein(s) and/or are oligosaccharides, and (2) a chitosan, in the manufacture of a medicament for intranasal delivery to an animal in order to raise an immune response.

These medicaments are preferably for the prevention and/or treatment of a disease caused by a *Neisseria* (e.g. meningitis, septicaemia, gonorrhoea etc.). They are preferably for intranasal administration. They preferably comprise capsular saccharides from at least two (i.e. 2, 3 or 4) of serogroups A, C, W135 and Y of *N. meningitidis*.

Definitions

The term "comprising" means "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Meningococcal Serogroup C Vaccine

A $CRM_{197}$ meningococcal C oligosaccharide conjugate [6,9] was administered intranasally at 1 µg per dose (measured as saccharide) to mice using N-trimethyl-chitosan chloride [179] and/or LT-K63 adjuvants. TMC was used as 8 µg per dose, and was prepared from chitosan ('Chitoclear', Primex ehf, Iceland) from shrimp shells (94.5% acetylated) with 18.9% substitution. LT-K63 was used at 1 or 0.1 µg per dose. Unanesthesized female BALB/c were immunized intranasally on days 0, 21, 35 with the formulations in 10 µl volumes (5 µl per nostril). Serum samples were taken before and after each immunization. Nasal washes were taken ten days after the third immunization. IgG and IgA antibody titers specific for MenC and for LT were determined by ELISA [180].

Figure 14A:
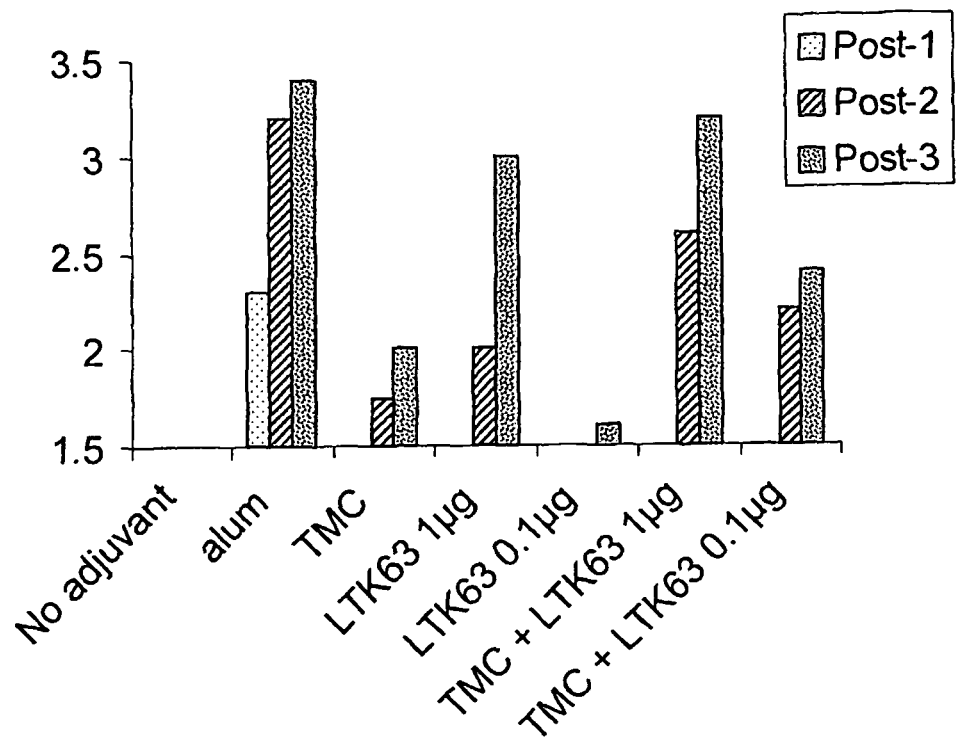
FIG. 14 shows IgG ELISA titres (14A) and bactericidal titres (14B) using TMC and/or LT-K63.
Figure 14B:
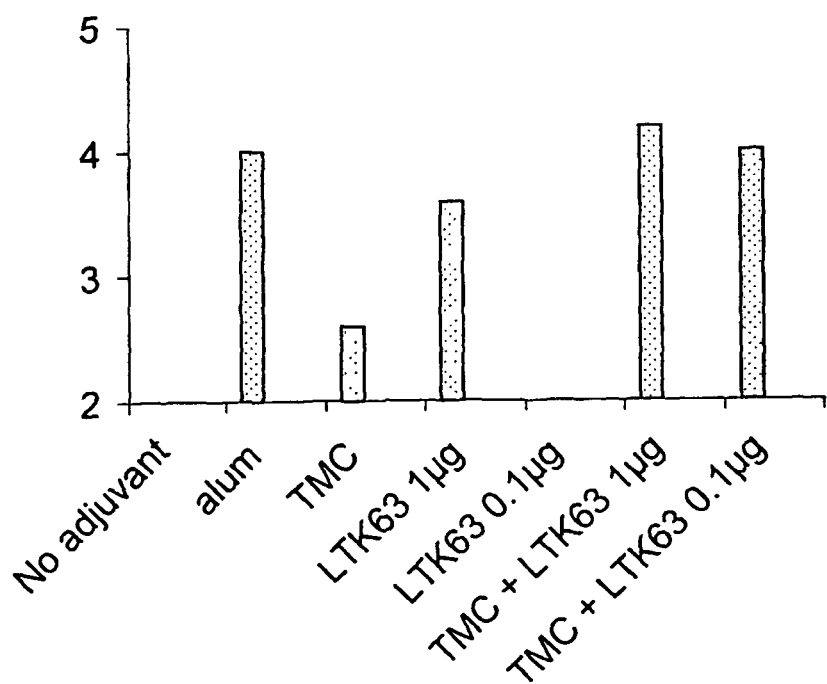
Figure 15A:
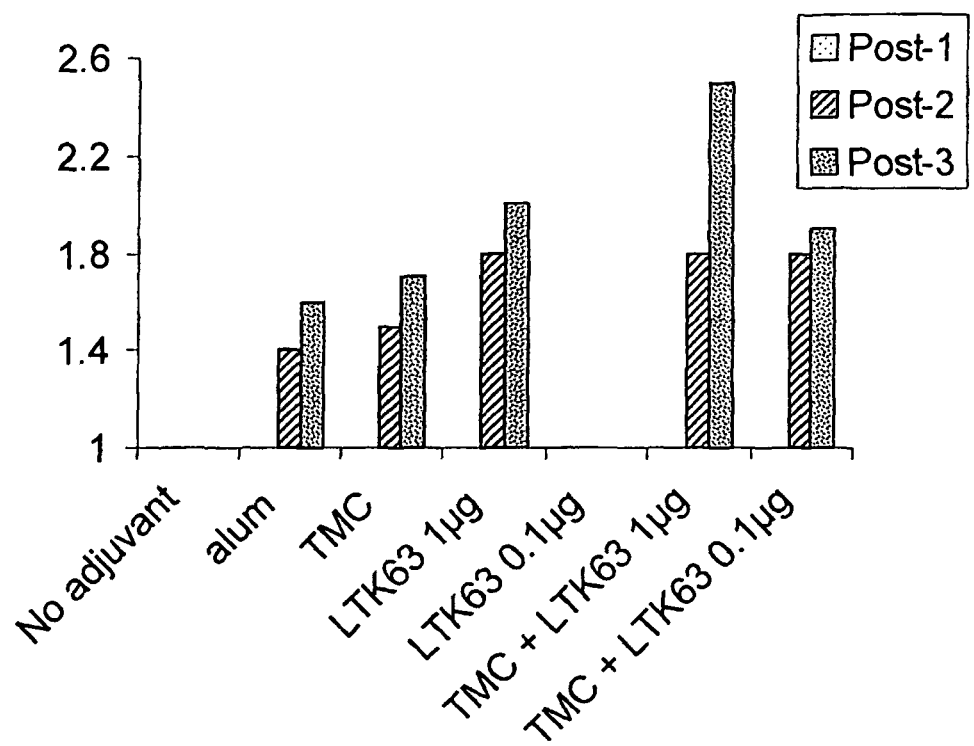
FIG. 15 shows IgA titres in serum (15A) and nasal washes (15B) for the same experiments.
Figure 15B:
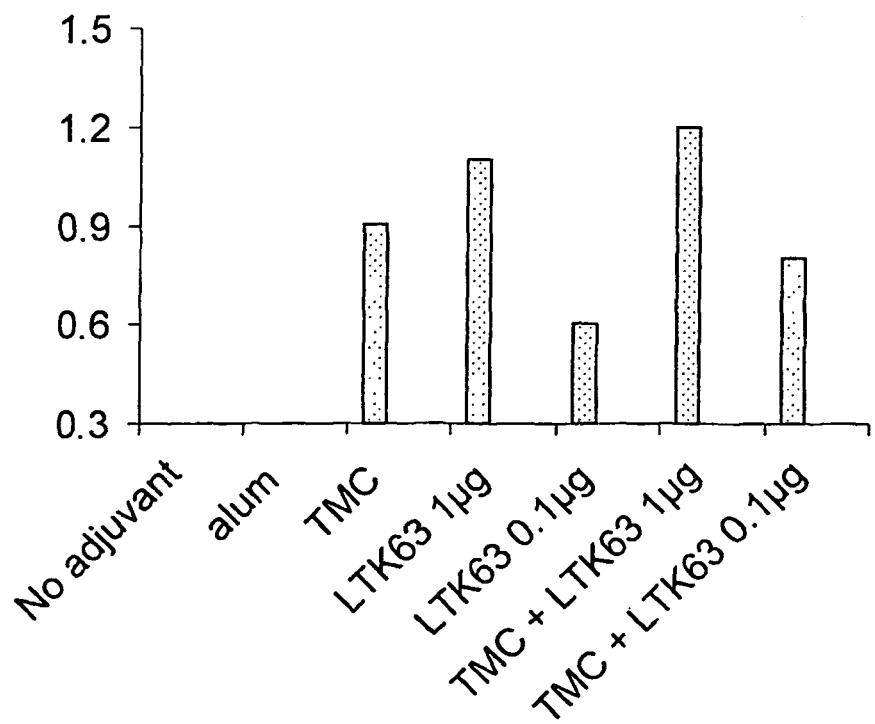
Figure 16:
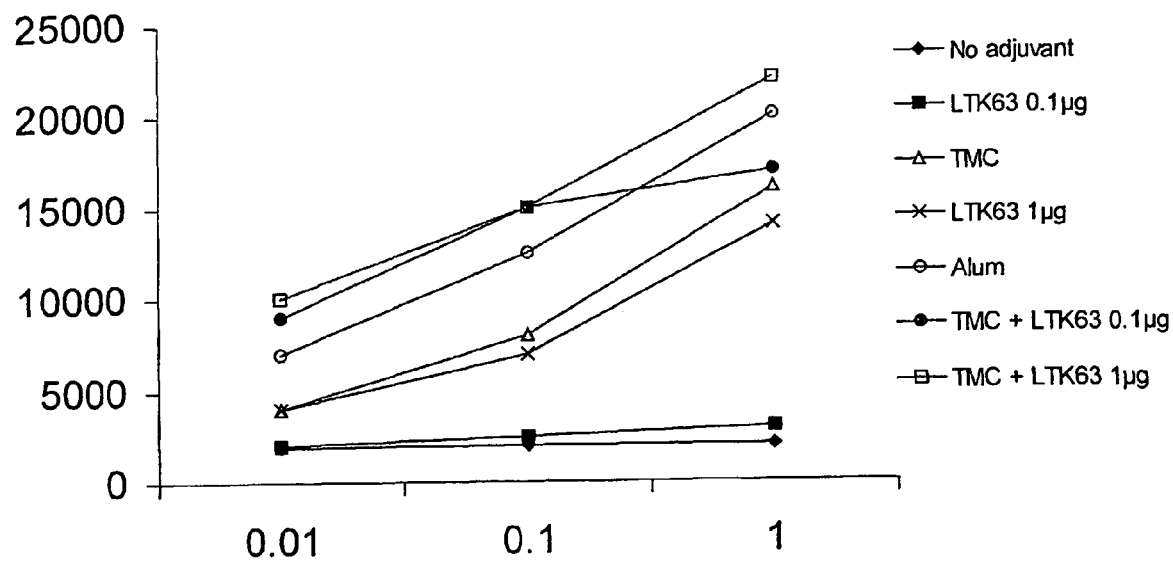
FIG. 16 shows results of a spleen proliferation assay varying with $CRM_{197}$ concentration (μg/ml).

Serum IgG responses are shown in FIG. 14: (A) ELISA and (B) bactericidal (log scale). FIG. 15 shows IgA titres in (A) serum and (B) nasal washes. FIG. 16 shows the results of a spleen proliferation assay.

The data show that TMC alone enhances immunogenicity and also that TMC enhances immunogenicity when co-administered with LT-K63 adjuvant. The mice receiving 1 µg LT-K63 and TMC combined achieved IgG titres comparable to those obtained by subcutaneous immunisation. Moreover, the combined adjuvants at both doses gave equal or better serum bactericidal antibody responses than subcutaneous immunisation. Subcutaneous immunisation did not give rise to a MenC-specific IgA response in nasal washes.

TMC and LTK-63 are thus effective intranasal adjuvants for MenC saccharide antigen, either alone or in combination. Advantageously, the addition of TMC to LT-K63 allows the dose of LT-K63 to be reduced by 90% without loss of immunogenicity. TMC thus allows components with potential residual toxicity to be reduced without loss of immunogenicity.

Similar experiments were performed using unmethylated 'Chitoclear' chitosan as adjuvant. Mice received the same conjugate antigen at 2.5 µg saccharide per dose, but with LT-K63 (1 µg) and/or chitosan (10 or 20 µg), by the same route. Six groups of mice were used:

|  | Group | | | | | |
|---|---|---|---|---|---|---|
|  | 1 | 2 | 3 | 4 | 5 | 6 |
| Alum | + | − | − | − | − | − |
| LT-K63 | − | + | − | − | + | + |
| Chitosan | − | − | 10 µg | 20 µg | 10 µg | 20 µg |
| Route | s.c. | i.n. | i.n. | i.n. | i.n. | i.n. |

Figure 17:
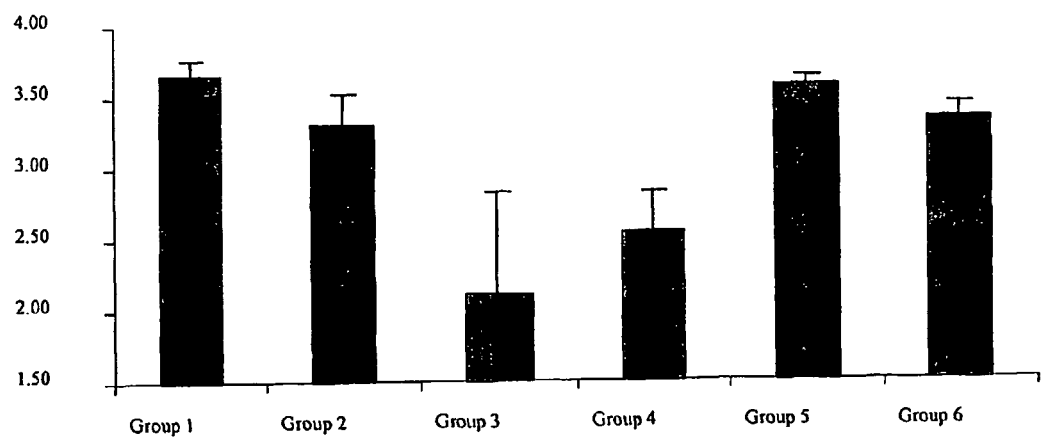
FIG. 17 shows serum IgG titres obtained after three doses of MenC antigen with chitosan adjuvant.
Figure 18:
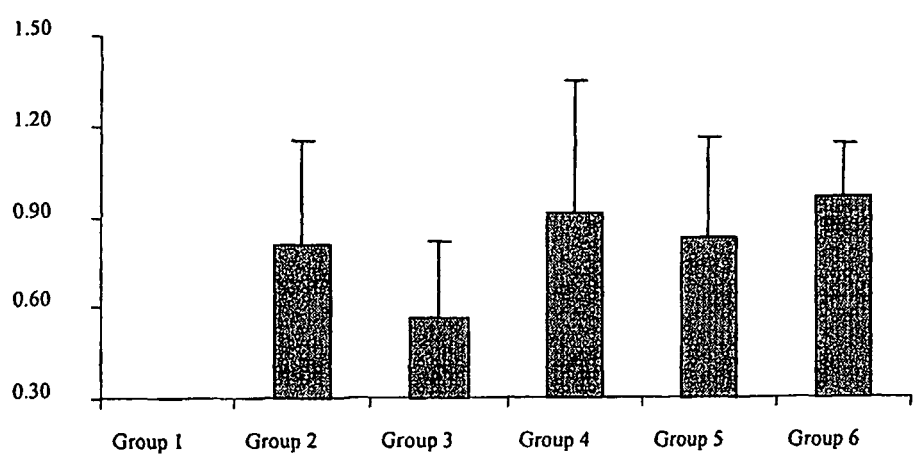
FIG. 18 shows nasal IgA titres for the same experiments.
Figure 19:
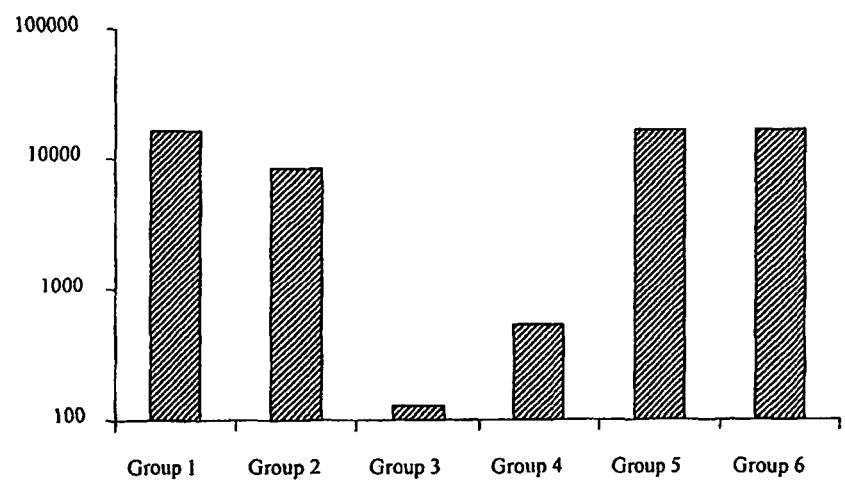
FIG. 19 shows serum bactericidal antibodies for the same experiments.

As shown in FIGS. 17 to 19, intranasal administration with LT-K63 and chitosan, in comparison to subcutaneous administration with alum, gave equivalent IgG and serum bactericidal responses, and resulted in nasal IgA responses.

Combined Vaccine

A combined ACWY composition of oligosaccharide conjugates was prepared using the materials described in reference 8. The composition was buffered at pH 7.4 with PBS. The concentration of each conjugate was:

| | Saccharide concentration (µg/ml) | $CRM_{197}$ concentration (µg/ml) |
|---|---|---|
| A | 487.50 | 1073.4 |
| C | 656.00 | 968.5 |
| W | 939.70 | 918.0 |
| Y | 583.70 | 837.1 |

The composition was administered intranasally to mice in 10 µl volumes (5 µl per nostril) without adjuvant or with one of the following mucosal adjuvants:

| Adjuvant | Concentration (µg/dose) |
|---|---|
| LT-K63 | 1 |
| Chitosan | 25 |
| Trimethylchitosan (TMC) | 25 |
| LT-K63 + TMC | As above (1 + 25) |

For comparison, the same antigen composition was administered subcutaneously with an aluminium hydroxide adjuvant.

As a control, the MenC conjugate alone was administered with the same adjuvants by the same routes at an equivalent concentration as the MenC in the combination composition.

Ten groups of mice therefore received the following compositions:

| # | Antigen | Antigen (µg) | Adjuvant | Adjuvant (µg) |
|---|---|---|---|---|
| 1 | ACWY | 4 | Alum (s.c.) | 500 |
| 2 | C | 1 | Alum (s.c.) | 500 |
| 3 | ACWY | 4 | — | — |
| 4 | C | 1 | — | — |
| 5 | ACWY | 4 | LTK63 | 1 |
| 6 | C | 1 | LTK63 | 1 |
| 7 | ACWY | 4 | TMC | 25 |
| 8 | C | 1 | TMC | 25 |
| 9 | ACWY | 4 | TMC + LTK63 | 25 + 1 |
| 10 | C | 1 | TMC + LTK63 | 25 + 1 |

Figure 1:
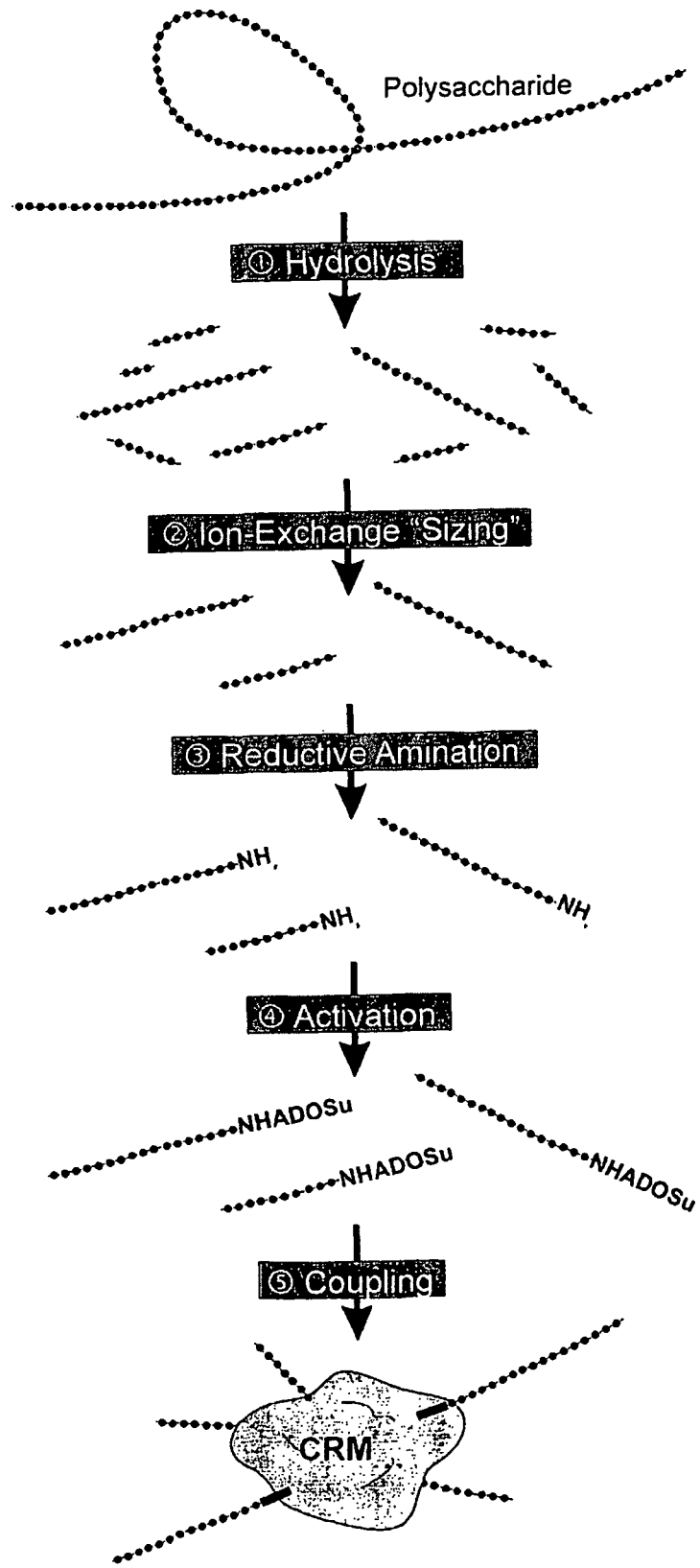
FIG. 1 illustrates the preparation of an oligosaccharide conjugate.
Figure 2:
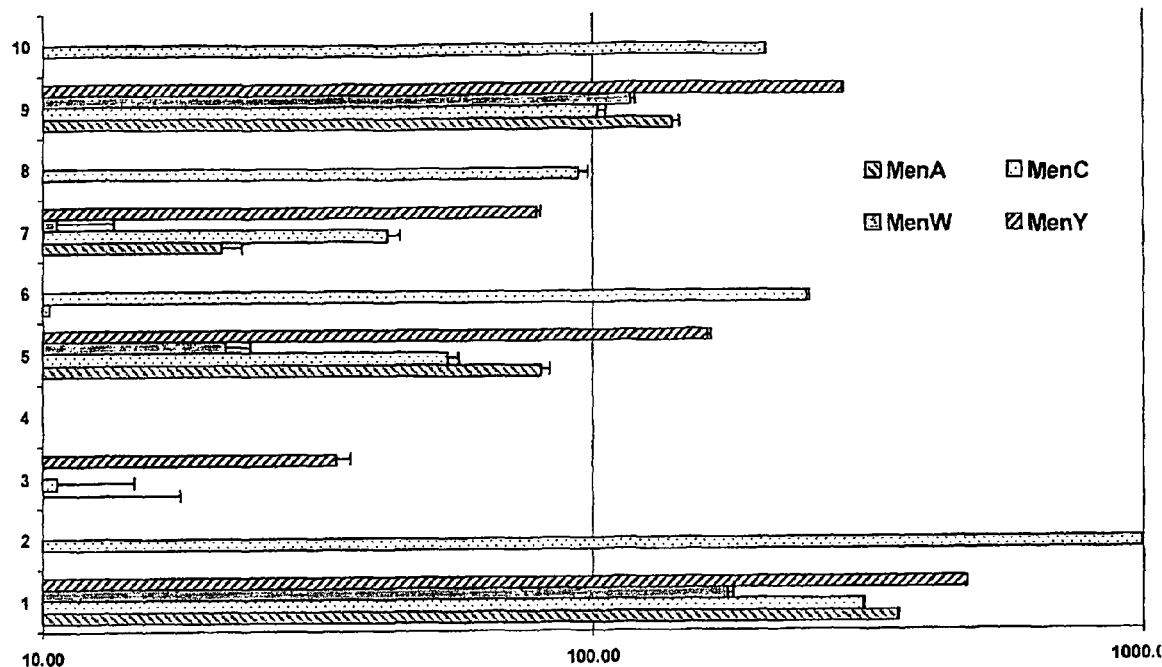
FIGS. 2, 5 & 8 shows serum IgG data from the examples.

In a first set of experiments, serum IgG levels following 3 intranasal doses (subcutaneous for alum) were as follows, expressed as GMT (MEU/ml)±standard deviation (FIG. 2):

| # | Anti-MenA | Anti-MenC | Anti-MenW | Anti-MenY |
|---|---|---|---|---|
| 1 | 356 ± 2.5 | 310 ± 2 | 176 ± 4 | 479 ± 1 |
| 2 | 2 | 996 ± 1 | 2 | 2 |
| 3 | 10 ± 8 | 11 ± 4 | 4 ± 5 | 34 ± 2 |
| 4 | 2 | 3 ± 3 | 2 | 2 |
| 5 | 81 ± 3 | 54 ± 3 | 22 ± 2 | 162 ± 2 |
| 6 | 10 | 246 ± 2 | 7 | 8 |
| 7 | 21 ± 2 | 42 ± 2 | 11 ± 3 | 79 ± 1 |
| 8 | 2 | 94 ± 4 | 2 | 2 |
| 9 | 140 ± 4 | 103 ± 4 | 118 ± 2 | 285 ± 2 |
| 10 | 2 | 205 ± 1 | 2 | 2 |

The same animals were tested for serum bactericidal antibodies in the presence of baby rabbit complement. Strains used were A-F6124, C-C11, W135-5554 and Y-240539

Figure 3:
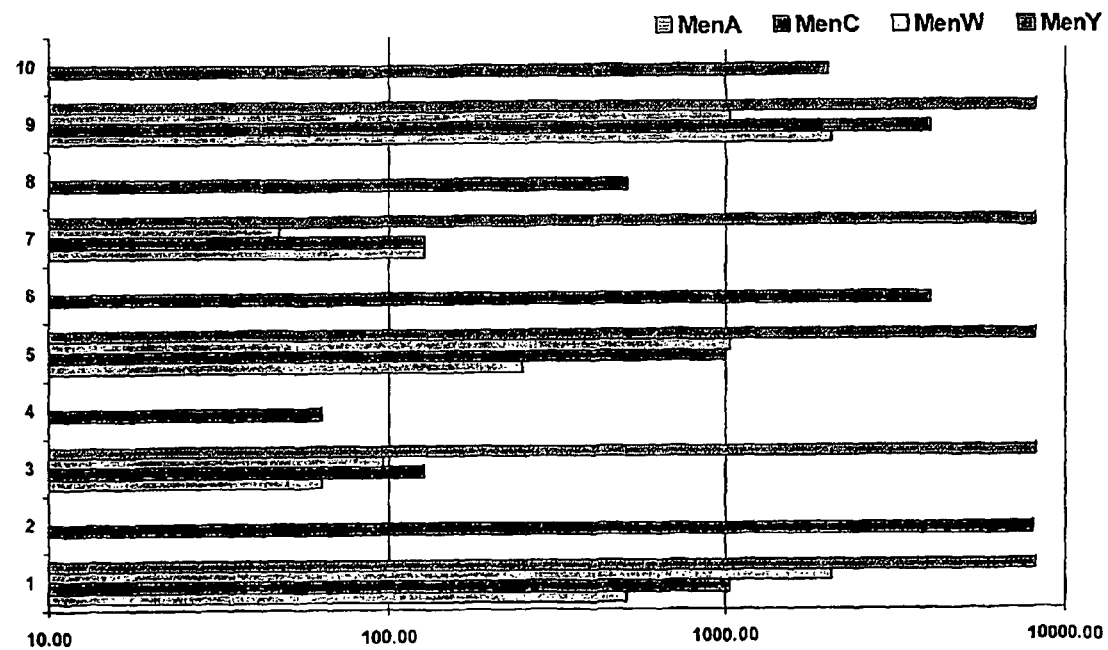
FIGS. 3, 6 & 9 shows serum BCA data from the examples.

Results were as follows (FIG. 3):

| # | Anti-MenA | Anti-MenC | Anti-MenW | Anti-MenY |
|---|---|---|---|---|
| 1 | 512 | 1024 | 2048 | 8192 |
| 2 | — | 8192 | — | — |
| 3 | 64 | 128 | 96 | 8192 |

-continued

| # | Anti-MenA | Anti-MenC | Anti-MenW | Anti-MenY |
|---|---|---|---|---|
| 4 | — | 64 | — | — |
| 5 | 256 | 1024 | 1024 | 8192 |
| 6 | — | 4096 | — | — |
| 7 | 128 | 256 | 48 | 8192 |
| 8 | — | 512 | — | — |
| 9 | 2048 | 4096 | 1024 | 8192 |
| 10 | — | 2048 | — | — |

Figure 4A:
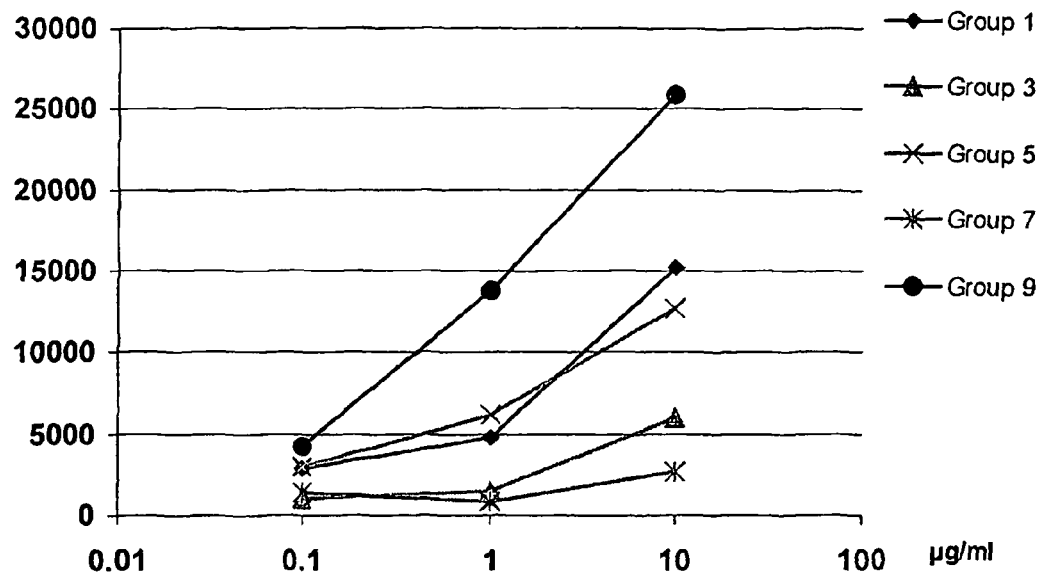
FIGS. 4, 7 & 10 shows spleen proliferation data from the examples.
Figure 4B:
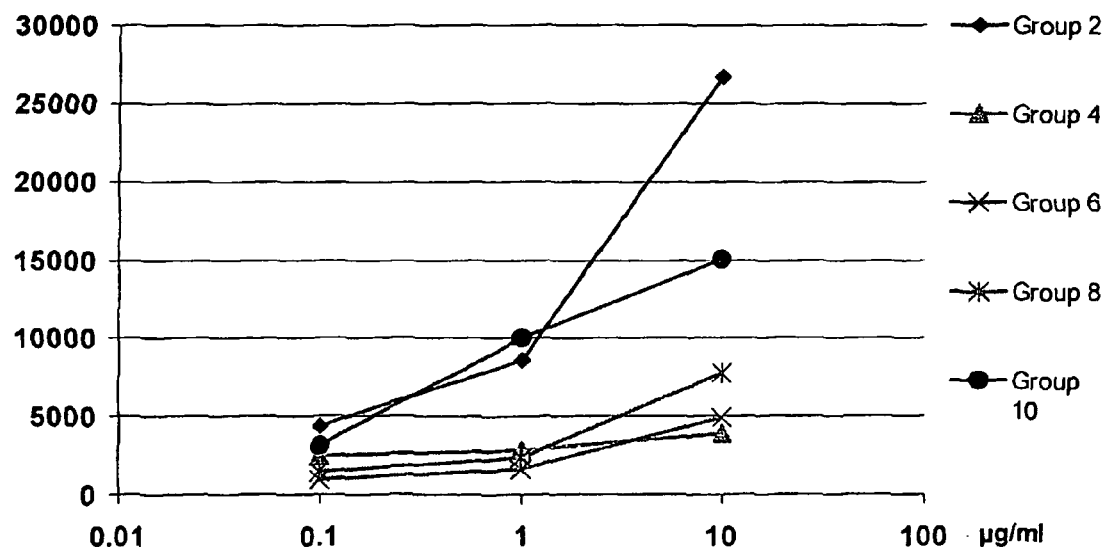

Proliferation on cells in the spleen was also tested for the same 10 groups. Results for odd-numbered groups, which received MenACWY antigens, are shown in FIG. 4A; even-numbered groups, which received MenC only, are in FIG. 4B.

In a second set of experiments, mice received 20 μl of the following ACWY compositions (each antigen as 2 μg saccharide) intranasally, except for group 1 which received it subcutaneously:

| # | Adjuvant | Adjuvant (μg) |
|---|---|---|
| 1 | Alum (s.c.) | 500 |
| 2 | Alum (i.n.) | 500 |
| 3 | LTK63 | 1 |
| 4 | TMC | 61 |
| 5 | TMC | 122 |
| 6 | LTK63 + TMC | 1 + 61 |
| 7 | LTK63 + TMC | 1 + 122 |
| 8 | Chitosan | 61 |
| 9 | Chitosan | 122 |
| 10 | LTK63 + chitosan | 1 + 61 |
| 11 | LTK63 + chitosan | 1 + 122 |

Figure 5:
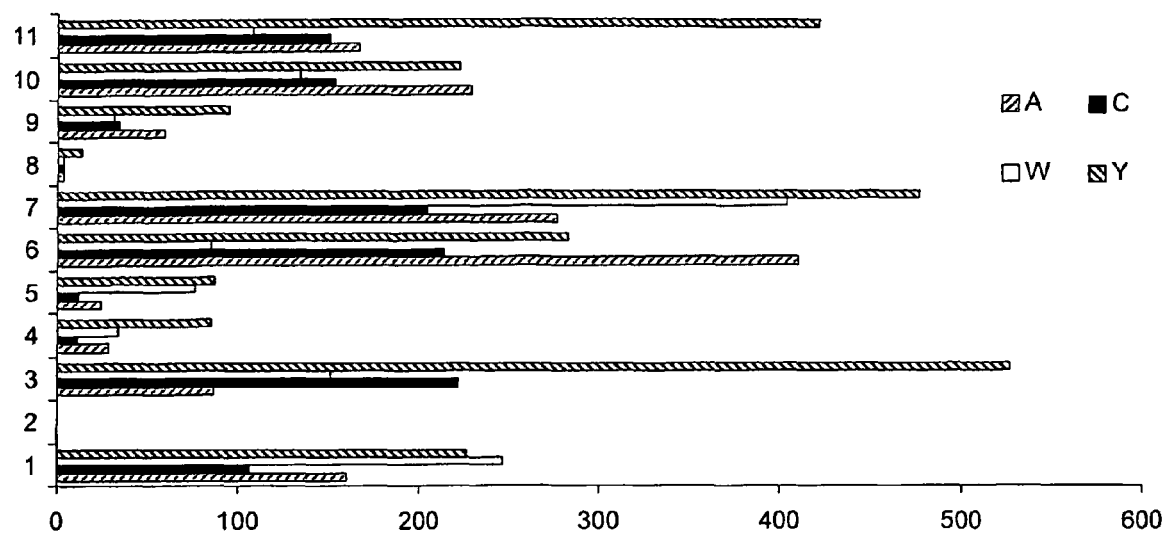
Figure 6:
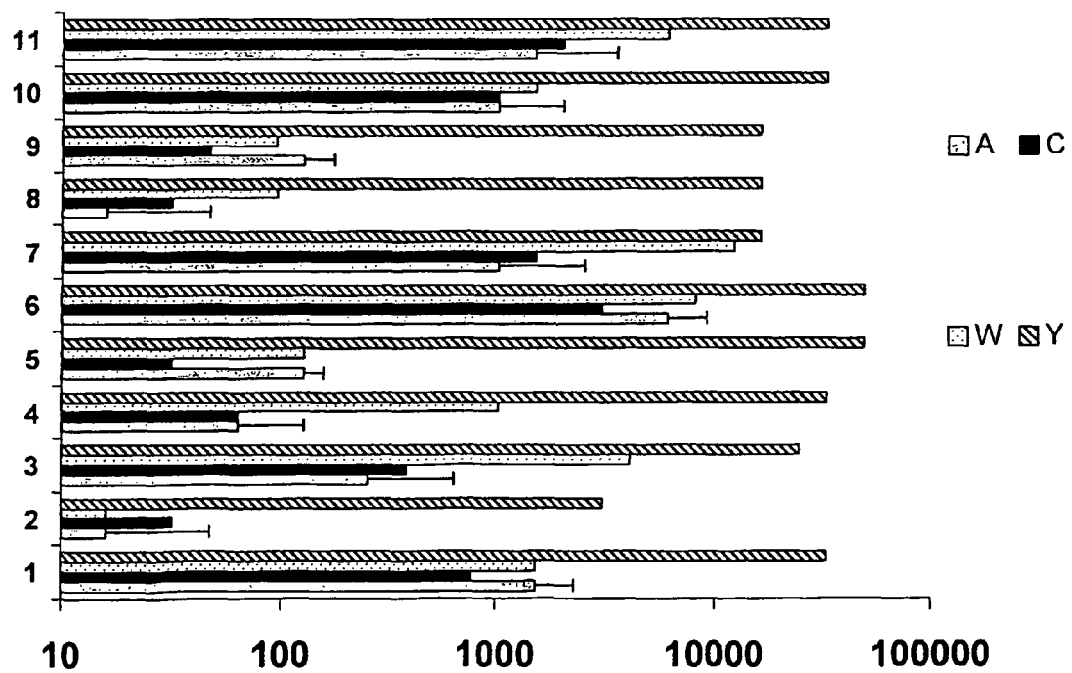
Figure 7A:
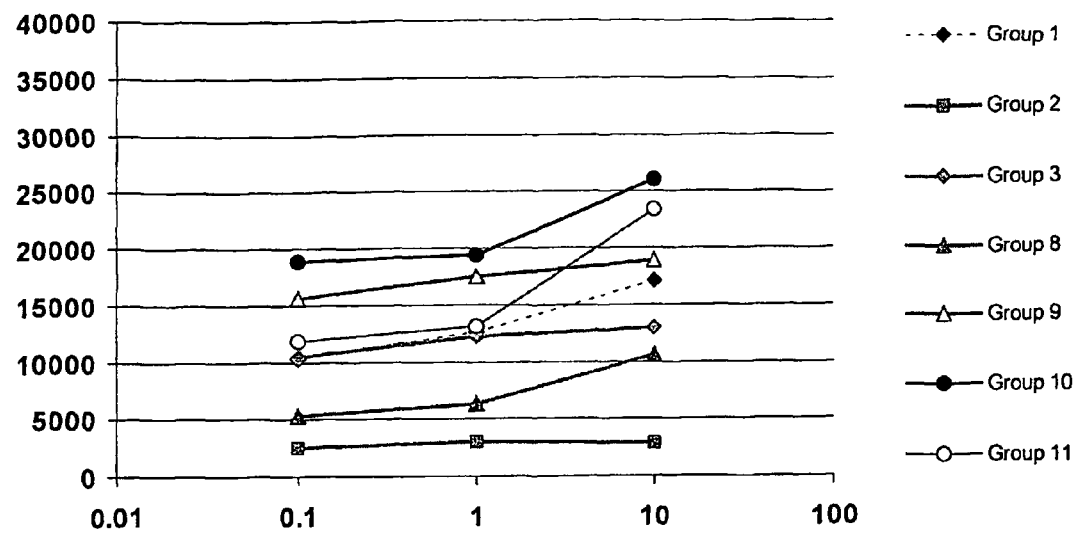
Figure 7B:
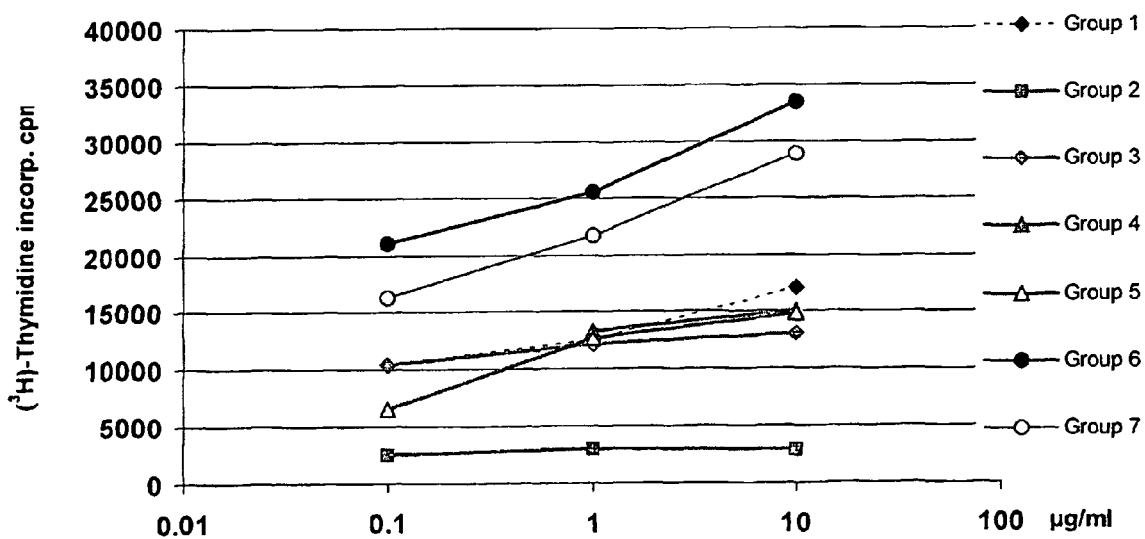

Serum IgG after three immunisations are shown in FIG. 5, serum BCA are shown in FIG. 6, and cell proliferation is shown in FIGS. 7A & 7B.

In a third set of similar experiments, mice received 201 μl of the following ACWY compositions (each antigenn as 2 μg saccharide) intranasally, except for group 1 which received it subcutaneously:

| # | Adjuvant | Adjuvant (μg) |
|---|---|---|
| 1 | Alum (s.c.) | 500 |
| 2 | — | — |
| 3 | LTK63 | 1 |
| 4 | LTK63 | 0.1 |
| 5 | TMC | 61 |
| 6 | LTK63 + TMC | 1 + 61 |
| 7 | LTK63 + TMC | 0.1 + 61 |
| 8 | Chitosan | 61 |
| 9 | LTK63 + Chitosan | 1 + 61 |
| 10 | LTK63 + Chitosan | 0.1 + 61 |

Figure 8:
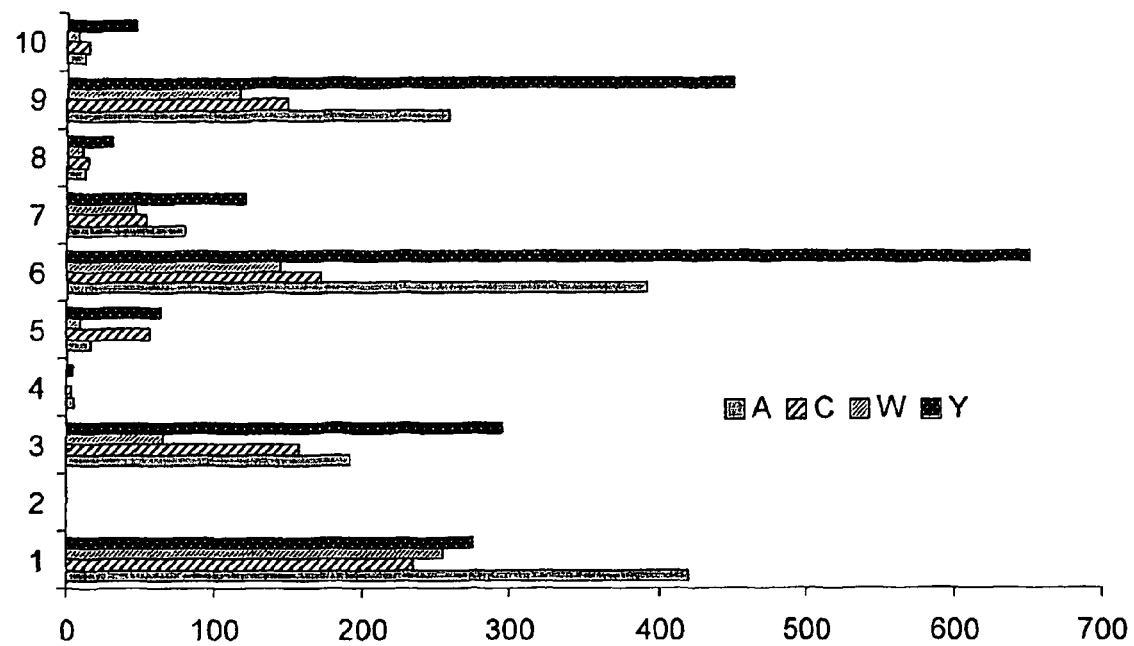
Figure 9:
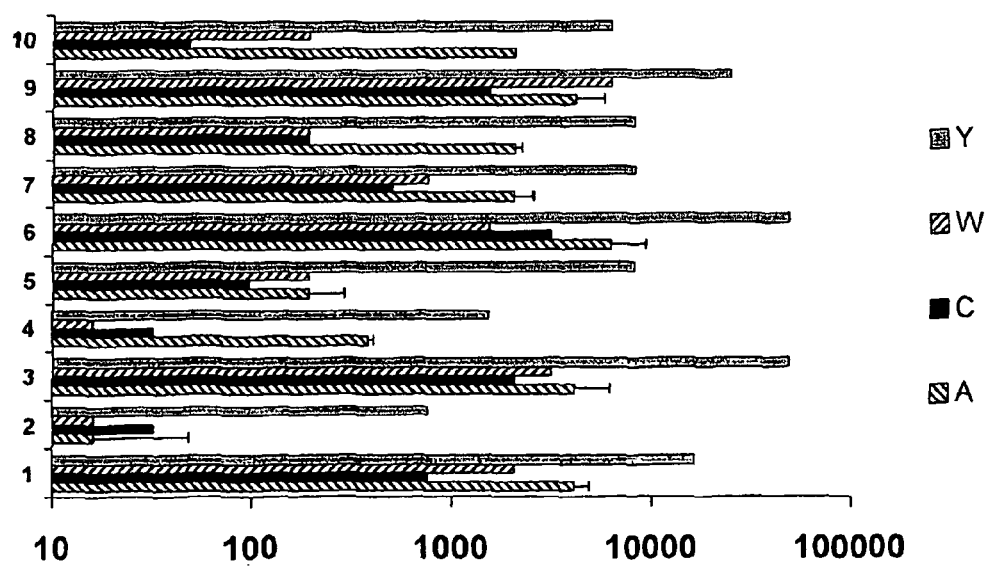
Figure 10A:
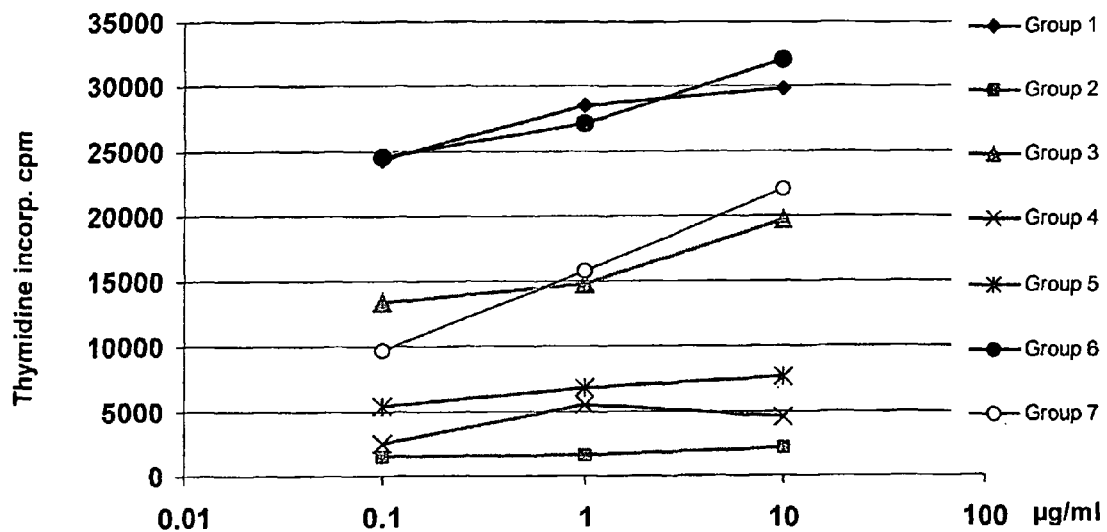
Figure 10B:
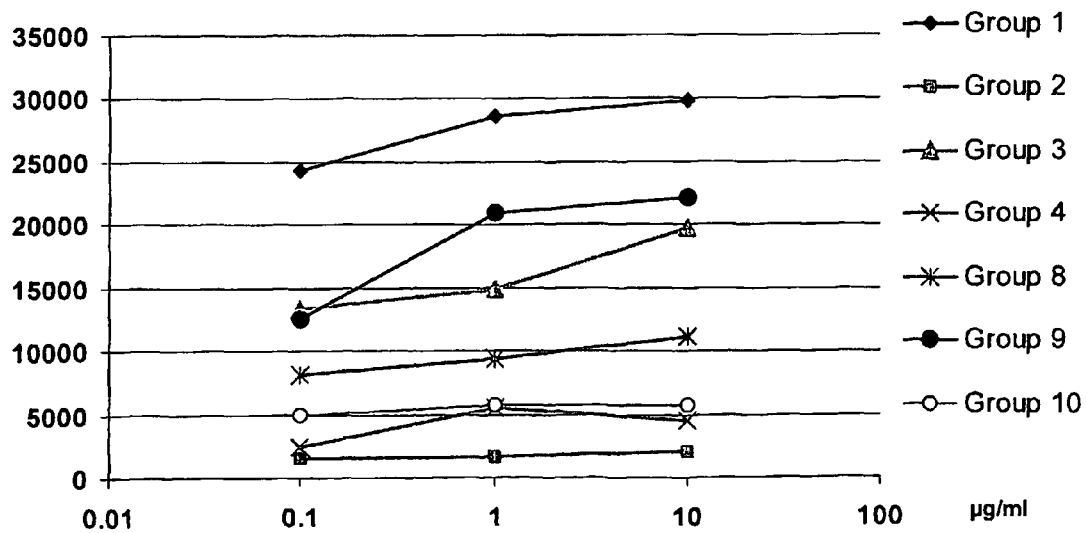
Figure 11:
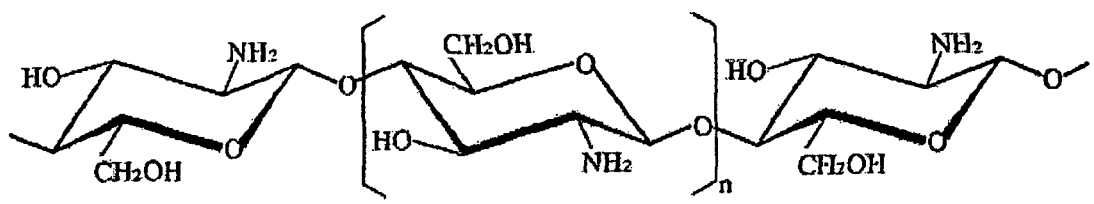
FIGS. 11 to 13 show the repeating structures of (11) chitosan (12) chitin and (13) trimethylchitosan.
Figure 12:
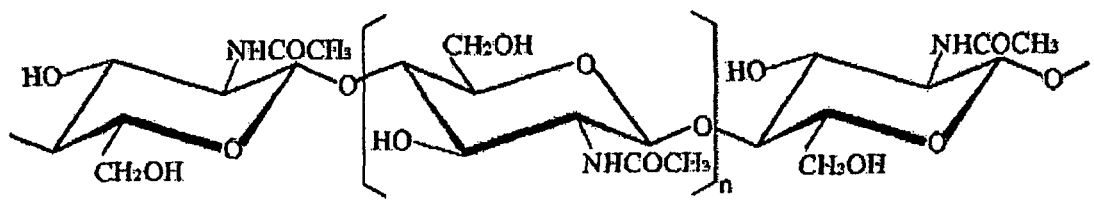
Figure 13:
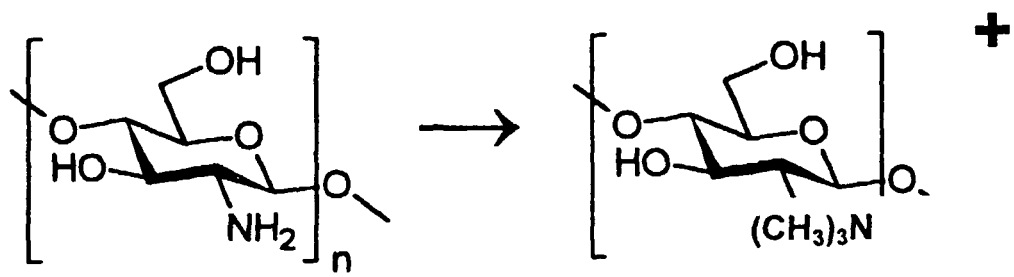

Serum IgG after three immunisations are shown in FIG. 8, serum BCA are shown in FIG. 9, and cell proliferation is shown in FIGS. 10A & 10B.

Thus both LTK63 and TMC, and particularly the pairing thereof, are highly effective adjuvants for intranasal delivery of a combined vaccine against meningococcal serogroups A, C, W135 and Y.

It will be understood that the invention has been described by way of example only and modifications may be made whilst remaining within the scope and spirit of the invention.
References (The Contents of Which Are Hereby Incorporated in Full)

[1] *Vaccines* (Plotkin & Orenstein) 3rd edition (1999) ISBN 0-7216-7443-7.
[2] Armand et al. (1982) *J. Biol. Stand.* 10:335-339.
[3] Cadoz et al. (1985) *Vaccine* 3:340-342.
[4] MMWR (1997) 46(RR-5) 1-10.
[5] Baklaic et al. (1983) *Infect. Immun.* 42:599-604.
[6] Costantino et al. (1992) *Vaccine* 10:691-698.
[7] WO02/00249.
[8] WO 03/007985.
[9] Costantino et al. (1999) *Vaccine* 17:1251-1263.
[10] Frash (1990) p. 123-145 of *Advances in Biotechnological Processes* vol. 13 (eds. Mizrahi & Van Wezel)
[11] Inzana (1987) *Infect. Immun.* 55:1573-1579.
[12] International patent application PCT/IB03/01436.
[13] Ravenscroft et al. (1999) *Vaccine* 17:2802-2816.
[14] Ramsay et al. (2001) *Lancet* 357(9251):195-196.
[15] Lindberg (1999) *Vaccine* 17 Suppl 2:S28-36.
[16] Buttery & Moxon (2000) *J R Coll Physicians Lond* 34:163-168.
[17] Ahmad & Chapnick (1999) *Infect Dis Clin North Am* 13:113-133, vii.
[18] Goldblatt (1998) *J. Med. Microbiol.* 47:563-567.
[19] European patent 0477508.
[20] U.S. Pat. No. 5,306,492.
[21] WO98/42721.
[22] Dick et al. in *Conjugate Vaccines* (eds. Cruse et al.) Karger, Basel, 1989, Vol. 10, pp. 48-114.
[23] Hermanson *Bioconjugate Techniques*, Academic Press, San Diego (1996) ISBN: 0123423368.
[24] Anonymous (January 2002) *Research Disclosure*, 453077.
[25] Anderson (1983) *Infect Immun* 39(1):233-238.
[26] Anderson et al. (1985) *J Clin Invest* 76(1):52-59.
[27] EP-A-0372501.
[28] EP-A-0378881.
[29] EP-A-0427347.
[30] WO93/17712
[31] WO94/03208.
[32] WO98/58668.
[33] EP-A-0471177.
[34] WO91/01146
[35] Falugi et al. (2001) *Eur J Immunol* 31:3816-3824.
[36] WO00/56360.
[37] WO00/61761.
[38] WO99/42130
[39] WO96/40242
[40] Lees et al. (1996) *Vaccine* 14:190-198.
[41] WO95/08348.
[42] U.S. Pat. No. 4,882,317.
[43] U.S. Pat. No. 4,695,624.
[44] *Mol. Immunol.*, 1985, 22, 907-919
[45] EP-A-0208375
[46] WO00/10599
[47] Gever et al., Med. Microbiol. Immunol, 165:171-288 (1979).
[48] U.S. Pat. No. 4,057,685.
[49] U.S. Pat. Nos. 4,673,574; 4,761,283; 4,808,700.
[50] U.S. Pat. No. 4,459,286.
[51] U.S. Pat. No. 4,965,338.
[52] U.S. Pat. No. 4,663,160.
[53] U.S. Pat. No. 4,761,283.
[54] U.S. Pat. No. 4,356,170
[55] Lei et al. (2000) *Dev Biol (Basel)* 103:259-264.
[56] WO00/38711; U.S. Pat. No. 6,146,902.
[57] Almeida & Alpar (1996) *J. Drug Targeting* 3:455-467.
[58] Agarwal & Mishra (1999) *Indian J Exp Biol* 37:6-16.
[59] Walker (1994) *Vaccine* 12:387-400.
[60] Clements (1997) *Nature Biotech.* 15:622-623.
[61] McGhee et al. (1992) *Vaccine* 10:75-88.

[62] Michetti (1998) *J. Gastroenterol.* [Suppl X]:66-68.
[63] International patent application WO03/009869.
[64] Del Giudice et al. (1998) *Molecular Aspects of Medicine*, vol. 19, number 1.
[65] International patent application WO99/52549.
[66] International patent application WO01/21207.
[67] International patent application WO0 1/21152.
[68] International patent application WO99/27960.
[69] International patent application WO00/62800.
[70] Johnson et al. (1999) *Bioorg Med Chem Lett* 9:2273-2278.
[71] International patent application WO00/50078.
[72] Singh et al. (2001) *J. Cont. Rele.* 70:267-276.
[73] *Vaccine design: the subunit and adjuvant approach*, eds. Powell & Newman, Plenum Press 1995 (ISBN 0-306-44867-X.
[74] WO90/14837.
[75] U.S. Pat. No. 6,299,884.
[76] WO00/07621.
[77] WO99/44636.
[78] GB-2220221.
[79] EP-A-0689454.
[80] WO00/56358.
[81] EP-A-0835318.
[82] EP-A-0735898.
[83] EP-A-0761231.
[84] WO00/23105.
[85] WO99/11241.
[86] WO98/57659.
[87] WO96/09805 (see also U.S. Pat. No. 5,912,000).
[88] WO96/10421 (see also U.S. Pat. No. 6,048,536).
[89] WO97/01330.
[90] WO97/16208 (see also U.S. Pat. No. 6,136,606).
[91] WO97/20576 (see also U.S. Pat. No. 6,391,318).
[92] WO98/42374.
[93] WO01/35994.
[94] van der Lubben et al. (2001) *Eur. J. Pharm. Sci.* 14:201-207.
[95] Le Buanec et al. (2001) *Biomed. Pharmacother.* 55:316-320.
[96] Seferian & Martinez (2000) *Vaccine* 19:661-668.
[97] Jabbal-Gill et al. (1998) *Vaccine* 16:2039-2046.
[98] Marcinkiewicz et al. (1991) *Arch. Immunol. Ther. Exp. (Warsz)* 39:127-132.
[99] Singla & Chawla (2001) *J. Pharm. Pharmacol.* 53:1047-1067.
[100] Hwang et al. (2002) *J. Agric. Food Chem.* 50:1876-1882.
[101] He et al. (1999) *Int. J. Pharm.* 187:53-65.
[102] He et al. (1999) *J. Microencapsul.* 16:343-355.
[103] *The Comprehensive Sourcebook of Bacterial Protein Toxins* (Alouf & Freer) ISBN 0120530759.
[104] WO 02/079242.
[105] International patent application WO93/13202.
[106] European patent applications 0306618, 0322533 and 0322115.
[107] European patent 0396964.
[108] Northrup & Fauci (1972) *J. Infect. Dis.* 125:672ff.
[109] Elson & Ealding (1984) *J. Immunol.* 133:2892ff and 132:2736ff.
[110] International patent application WO95/17211.
[111] Del Giudice et al. (1998) *Molecular Aspects of Medicine*, vol. 19, number 1.
112. Park et al. (2000) Exp. Mol. Med. 32:72-8.
[113] International patent application WO98/18928.
[114] Pizza et al. (2000) *Int. J. Med. Microbiol.* 290:455-461.
[115] WO99/24578.
[116] WO99/36544.
[117] WO99/57280.
[118] WO00/22430.
[119] Tettelin et al. (2000) *Science* 287:1809-1815.
[120] Pizza et al. (2000) *Science* 287:1816-1820.
[121] WO01/52885.
[122] Bjune et al. (1991) *Lancet* 338(8775):1093-1096.
[123] Fukasawa et al. (1999) *Vaccine* 17:2951-2958.
[124] Rosenqvist et al. (1998) *Dev. Biol. Stand.* 92:323-333.
[125] WO96/14086.
[126] Covacci & Rappuoli (2000) *J. Exp. Med.* 19:587-592.
[127] WO93/18150.
[128] Covacci et al. (1993) *Proc. Natl. Acad. Sci. USA* 90:5791-5795.
[129] Tummuru et al. (1994) *Infect. Immun.* 61:1799-1809.
[130] Marchetti et al. (1998) *Vaccine* 16:33-37.
[131] Telford et al. (1994) *J. Exp. Med.* 179:1653-1658.
[132] Evans et al. (1995) *Gene* 153:123-127.
[133] WO96/01272 & WO96/01273, especially SEQ ID NO:6.
[134] WO97/25429.
[135] WO98/04702.
[136] Watson (2000) *Pediatr Infect Dis J* 19:331-332.
[137] Rubin (2000) *Pediatr Clin North Am* 47:269-285, v.
[138] Jedrzejas (2001) *Microbiol Mol Biol Rev* 65:187-207.
[139] Bell (2000) *Pediatr Infect Dis J* 19:1187-1188.
[140] Iwarson (1995) *APMIS* 103:321-326.
[141] Gerlich et al. (1990) *Vaccine* 8 Suppl:S63-68 & 79-80.
[142] WO93/24148.
[143] WO97/00697.
[144] Hsu et al. (1999) *Clin Liver Dis* 3:901-915.
[145] WO02/02606.
[146] Kalman et al. (1999) *Nature Genetics* 21:385-389.
[147] Read et al. (2000) *Nucleic Acids Res* 28:1397-406.
[148] Shirai et al. (2000) *J. Infect. Dis.* 181(Suppl 3):S524-S527.
[149] WO99/27105.
[150] WO00/27994.
[151] WO00/37494.
[152] WO99/28475.
[153] Ross et al. (2001) *Vaccine* 19:4135-4142.
[154] Sutter et al. (2000) *Pediatr Clin North Am* 47:287-308.
[155] Zimmerman & Spann (1999) *Am Fam Physician* 59:113-118, 125-126.
[156] Dreesen (1997) *Vaccine* 15 Suppl:S2-6.
[157] *MMWR Morb Mortal Wkly Rep* 1998 Jan. 16;47(1):12, 19.
[158] McMichael (2000) *Vaccine* 19 Suppl 1:S101-107.
[159] Schuchat (1999) *Lancet* 353(9146):51-6.
[160] WO02/34771.
[161] Dale (1999) *Infect Dis Clin North Am* 13:227-43, viii.
[162] Ferretti et al. (2001) *PNAS USA* 98: 4658-4663.
[163] Kuroda et al. (2001) *Lancet* 357(9264):1225-1240; see also pages 1218-1219.
[164] Anderson (2000) *Vaccine* 19 Suppl 1:S59-65.
[165] Kahn (2000) *Curr Opin Pediatr* 12:257-262.
[166] Crowe (1995) *Vaccine* 13:415-421.
[167] *J Toxicol Clin Toxicol* (2001) 39:85-100.
[168] Demicheli et al. (1998) *Vaccine* 16:880-884.
[169] Stepanov et al. (1996) *J Biotechnol* 44:155-160.
[170] Gustafsson et al. (1996) *N. Engl. J. Med.* 334:349-355.
[171] Rappuoli et al. (1991) *TIBTECH* 9:232-238.
[172] Charalambous & Feavers (2001) *J Med Microbiol* 50:937-939.
[173] Westerink (2001) *Int Rev Immunol* 20:251-261.
[174] Grothaus et al. (2000) *Vaccine* 18:1253-1263.
[175] WO00/56365.

[176] Gennaro (2000) *Remington: The Science and Practice of Pharmacy*. 20th ed ISBN: 0683306472
[177] WO01/30390.
[178] WO98/20734.
[179] Van der Lubben et al. (2002) *S T P Pharm. Sci.* 12:235-242.
[180] Baudner et al. (2002) *Infect. Immun.* 70:4785-4790

The invention claimed is:

1. An immunogenic composition, comprising (a) a capsular saccharide antigen from serogroup C of *N.meningitidis*, (b) a chitosan adjuvant, and (c) a detoxified mutant of *E. coli* heat-labile toxin.

2. An immunogenic composition for mucosal delivery, comprising capsular saccharides from at least two of serogroups A, C, W135 and Y of *N.meningitidis*, a chitosan adjuvant, and a detoxified mutant of *E.coli* heat-labile toxin.

3. The composition of claim 1, comprising (d) one or more further antigens or (e) one or more further adjuvants.

4. The composition of claims 1, 2 or 3, wherein the capsular saccharides are conjugated to carrier protein(s) or are oligosaccharides.

5. The composition of claim 3, wherein the capsular saccharides are oligosaccharides conjugated to carrier protein(s).

6. The composition of anyone of claims 1, 2, 3, or 5, comprising capsular saccharides from 2, 3, or 4 of serogroups A, C, W135 and Y of *N meningitidis*.

7. The composition of claim 6, comprising saccharides from serogroups A+C, A+W135, A+Y, C+W135, C+Y, W135+Y, A+C+W135, A+C+Y, C+W135+Y, A+C+W135+Y.

8. The composition of any one of claims 1, 2, 3, or 5, which is adapted or packaged for intranasal administration.

9. The composition of claim 8, in the form of a nasal spray or nasal drops.

10. The composition of claim 1, wherein the detoxified mutant of *E.coli* heat-labile toxin has a serine-to-lysine substitution at residue 63.

11. The composition of anyone of claims 1, 2, 3, or 5, wherein the composition further comprises an antigen which induces an immune response against *Haemophilus influenzae* or an antigen which induces an immune response against *Streptococcus pneumoniae*.

12. The composition of anyone of claims 1, 2, 3, or 5, further comprising an antigen which induces an immune response against *Haemophilus influenzae* and an antigen which induces an immune response against *Streptococcus pneumoniae*.

13. A kit comprising: (a) capsular saccharide from *N.meningitidis* serogroup A, in lyophilized form; (b) capsular saccharide(s) from one or more of *N.meningitidis* serogroups C, W135 and Y, in liquid form, (c) a chitosan adjuvant, and (d) a detoxified mutant of *E.coli* heat-labile toxin, wherein (a), (b), (c), and (d) are formulated such that, when combined, they are suitable for mucosal administration.

14. A method of raising an immune response in a patient, comprising administering to a patient a composition according to anyone of claims 1, 2, 3, or 5.

15. The method of claim 14, wherein the medicament is delivered intranasally.

* * * * *